United States Patent
Segall

(10) Patent No.: US 10,726,743 B2
(45) Date of Patent: Jul. 28, 2020

(54) MULTI-JUNCTIONAL BLEEDING SIMULATOR

(71) Applicant: Strategic Operations, Inc., San Diego, CA (US)

(72) Inventor: Stuart C. Segall, La Jolla, CA (US)

(*) Notice: Subject to any disclaimer, the term of this patent is extended or adjusted under 35 U.S.C. 154(b) by 271 days.

(21) Appl. No.: 15/859,112

(22) Filed: Dec. 29, 2017

(65) Prior Publication Data

US 2018/0190155 A1 Jul. 5, 2018

Related U.S. Application Data

(60) Provisional application No. 62/441,064, filed on Dec. 30, 2016.

(51) Int. Cl.
| | |
|---|---|
| G09B 23/28 | (2006.01) |
| G09B 23/30 | (2006.01) |
| A61M 1/00 | (2006.01) |
| A61B 17/00 | (2006.01) |
| A61F 13/02 | (2006.01) |
| A61B 17/12 | (2006.01) |

(52) U.S. Cl.
CPC ........ G09B 23/303 (2013.01); A61B 17/0057 (2013.01); A61M 1/0088 (2013.01); G09B 23/30 (2013.01); A61B 17/12122 (2013.01); A61F 13/0226 (2013.01); A61F 13/0276 (2013.01); A61L 2400/04 (2013.01)

(58) Field of Classification Search
CPC ....... G09B 23/28; G09B 23/30; G09B 23/303
USPC ............... 434/262, 265, 267, 268, 272, 274
See application file for complete search history.

(56) References Cited

U.S. PATENT DOCUMENTS

| | | |
|---|---|---|
| 2,213,270 A | 9/1940 | Chase |
| 2,752,697 A | 3/1956 | Lawall |
| 3,027,655 A | 4/1962 | Alderson |
| 3,852,893 A | 12/1974 | Smrcka |
| 4,331,426 A | 5/1982 | Sweeney |
| 5,397,237 A | 3/1995 | Dhont |
| 5,411,437 A | 5/1995 | Weber |
| 5,634,797 A | 6/1997 | Montgomery |
| 5,839,904 A * | 11/1998 | Bloom ................. G09B 23/285 434/268 |
| 6,234,804 B1 | 5/2001 | Young |
| 6,780,016 B1 | 8/2004 | Toly |
| 7,021,940 B2 | 4/2006 | Morris |
| 7,306,465 B2 * | 12/2007 | White ................. G09B 23/285 434/268 |

(Continued)

*Primary Examiner* — Kurt Fernstrom
(74) *Attorney, Agent, or Firm* — Enrique A. Monteagudo, Esq.

(57) ABSTRACT

The present invention, when used by a live actor, allows users to safely simulate hemorrhaging in some of the most challenging blood vessels in the most challenging anatomical locations such as the carotid artery, the axillary artery, and the inguinal artery. The present invention further provides the ability for users to safely perform hemorrhage control procedures, such as compression and ligation. The simulated wound of the present invention may be compressed to control hemorrhage. The simulated wound receptacle of the present invention may be packed with hemostatic or simple gauze to control hemorrhage. The simulated blood vessel of the device may be ligated with hemostats or other ligating instruments or material and bandaged with pressure dressings to control hemorrhage.

12 Claims, 21 Drawing Sheets

(56) References Cited

U.S. PATENT DOCUMENTS

| | | | |
|---|---|---|---|
| 7,621,749 B2* | 11/2009 | Munday | A61M 5/427 |
| | | | 434/262 |
| 7,857,626 B2 | 12/2010 | Toly | |
| 7,887,330 B2 | 2/2011 | King | |
| 8,221,129 B2* | 7/2012 | Parry | G09B 23/30 |
| | | | 434/272 |
| 8,342,852 B2 | 1/2013 | King | |
| 8,382,485 B2 | 2/2013 | Bardsley | |
| 8,408,920 B2* | 4/2013 | Speller | G09B 23/285 |
| | | | 434/267 |
| 8,840,403 B2 | 9/2014 | Segall | |
| 10,217,380 B2* | 2/2019 | Parry | G09B 23/281 |
| 10,354,556 B2* | 7/2019 | Hofstetter | G09B 23/303 |
| 2007/0292829 A1 | 12/2007 | King | |
| 2009/0011394 A1* | 1/2009 | Meglan | G09B 23/28 |
| | | | 434/268 |
| 2013/0078604 A1 | 3/2013 | King | |
| 2016/0171911 A1* | 6/2016 | Parry, Jr. | G09B 23/30 |
| | | | 434/268 |
| 2017/0193858 A1* | 7/2017 | Segall | G09B 23/303 |

* cited by examiner

MULTI-JUNCTIONAL BLEEDING SIMULATOR

RELATED APPLICATIONS

This application claims the benefit of priority to U.S. Provisional Patent Application Ser. No. 62/441,064 filed on Dec. 30, 2016, titled "Multi-Junctional Bleeding Simulator".

FIELD OF INVENTION

The present invention relates generally to casualty simulation and medical response team training systems. The present invention is more particularly, though not exclusively, a simulated wound apparatus allowing the wearer to simulate injuries for purposes of casualty simulation and medical response training.

BACKGROUND OF INVENTION

Hemorrhage is the leading cause of preventable death on the battlefield. For the injured having potentially survivable wounds, ninety percent die from uncontrolled hemorrhage. The majority of combat fatalities occur forward of a medical treatment facility. To raise the probability of survival from a bleeding wound so the injured may reach a medical treatment facility, the hemorrhage must be controlled immediately. To stop the bleeding, first responders are taught to find the wound and to stop the bleeding by occluding the blood vessel by compression or ligation. By applying direct pressure to the wound, it is possible the damaged blood vessel may be compressed closed. Alternatively, the damaged blood vessel may be compressed upstream with a tourniquet to cut off blood flow to the damaged blood vessel. Additionally, the wound may be compacted with material to obstruct the damaged blood vessel or the damaged blood vessel may be directly ligated. Under the extreme conditions and pressures of a combat zone, proper training is needed to ensure the correct procedure is performed to stop a hemorrhage and to save a life.

As is well known, and widely accepted, partial task simulators and training aids can be very effective for teaching individuals how to perform a wide variety of different tasks. More specifically, they can be extremely helpful for teaching an individual how to perform certain medical procedures during a life-threatening, emergency situation. In this context, and of particular importance for the present invention, are those medical procedures that are required for hemorrhage control in a combat zone. The import here is two-fold. Firstly, the partial task simulator should effectively augment the educational background that is necessary to assess an emergency situation. Secondly, it should serve as a tool with which a person can learn how to respond to an emergency situation by properly performing essential life-saving tasks. The efficacy of any partial task simulator or training aid, however, is dependent on the realism it provides and its ability to simulate or mimic an environment where the task is to be actually performed.

With the above in mind, a catastrophic event presents a situation wherein the proper training of emergency medical personnel can be invaluable. Regardless whether the event is the result of an accident, a natural disaster or some form of combat, the consequence of a first response to the event may make the difference between life and death. In such instances, the ability of medical personnel to rapidly and reliably attend to wounds and injuries is of crucial importance. Practice on partial task simulators such as medical mannequins, while valuable as teaching aids, are limited by the mannequin's immobility, weight, expense and minimal interaction with the medical personnel.

In light of the above, it is an object of the present invention to provide a device for realistically and dynamically simulating the wounds and injuries on a person (e.g., role player, actor) that can be received during a traumatic event. Another object of the present invention is to provide a device that effectively functions as a training aid to teach a person how to treat the wounds and injuries that can be received by a person during a traumatic event. Another object of the present invention is to provide a device that effectively functions as a training aid that allows verbal and gesticular interaction between a live human wearing the device and a first responder who is treating the person wearing the device. Still another object of the present invention is to provide a training aid for teaching how to treat wounds and injuries that is easy to use, is simple to manufacture and is comparatively cost effective.

SUMMARY OF INVENTION

The Multi-Junctional Bleeding Simulator of the present invention is designed as a human worn partial task hemorrhage control simulator. The Multi-Junctional Bleeding Simulator is designed to be worn in one of three positions as follows: bilateral anterio-frontal-pericervical ("neck junction"), bilateral axillary ("axillary junction"), and bilateral anterior-inguinal ("inguinal junction"). The neck junction is just forward of the junction of the neck and the trunk of the body on both left and right sides. The axillary junction is the junction of the arm and flank around the armpit on both the left and ride side. The inguinal junction is the front side of the junction of the leg and the pelvis to the side of the genital on both left and right side. The placement of the device at the neck junction may simulate a severed carotid artery. The placement of the device at the axillary junction may simulate a severed axillary artery. The placement of the device at the inguinal junction may simulate a severed inguinal artery.

The Multi-Junctional Bleeding Simulator, when used by a live actor, allows users to safely simulate hemorrhaging in some of the most challenging blood vessels in the most challenging anatomical locations. The Multi-Junctional Bleeding Simulator further provides the ability for users to safely perform hemorrhage control procedures, such as compression and ligation. The simulated wound of the device may be compressed with emergency trauma dressing to control hemorrhage. The simulated wound receptacle of the device may be packed with hemostatic gauze or simple gauze to control hemorrhage. The simulated blood vessel of the device may be ligated with hemostats or other ligating instruments or material and bandaged with pressure dressings to control hemorrhage.

In an embodiment of the Multi-Junctional Bleeding Simulator of the present invention, the Multi-Junctional Bleeding Simulator includes a top layer of silicone and a bottom layer of silicone adhered around the margins to create a receptacle, wherein the silicone layers simulate human skin. The top layer of silicone includes an opening simulating a wound to the body such as an abrasion, an excoriation, a hematoma, a laceration, an incision, a puncture wound, a contusion, a crushing injury, or a ballistic trauma. Penetrating through the bottom layer is a silicone tube with a first end and a second end. The first end of the tube penetrates through the bottom layer of silicone and resides in the receptacle to simulate a damaged blood vessel. The second end of the tube is attached to a blood pumping system that supplies blood to the tube to simulate a bleeding damaged blood vessel. The elasticity of the tube allows for the compression and/or ligation to occlude the tube. The receptacle allows the compaction of material into the receptacle to occlude the opening of the tube.

In an alternative embodiment of the Multi-Junctional Bleeding Simulator of the present invention, the tubing of the Multi-Junctional Bleeding Simulator may be replaced with a tubing system. The tubing system includes a primary tube, a feed tube, and an exhaust tube. The primary tube penetrates the bottom layer of silicone and resides in the receptacle. Attached to the primary tube, outside the receptacle, is a Y-connector. The main branch of the Y-connector is attached to the primary tube, the first branch of the Y-connector is connected to the feed tube, and a bypass valve is attached to the second branch of the Y-connector. Attached to the bypass valve is the exhaust tube. The bypass valve is normally closed and fully opens only when a predetermined pressure is met. The bypass valve also has a cracking pressure which opens the bypass valve a small amount. Fluid flow through the exhaust tube will indicate to the user that the proper application of pressure was applied to the wound to slow or stop the bleeding.

It is contemplated that the Multi-Junctional Bleeding Simulator of the present invention may include Multi-Junctional Attachment Unit that facilitates the attachment of the Multi-Junctional Bleeding Simulator to various locations on a live actor. The Multi-Junctional Attachment Unit includes an adjustable limb strap, a neck strap, and an extended strap. The Multi-Junctional Attachment Unit with the adjustable limb strap facilitates attachment to the axillary and inguinal junctions, the neck strap facilitates attachment to the neck junction, and the extended strap facilitates the attachment to the axillary junction and the inguinal junction of a live actor. The Multi-Junctional Attachment Device includes a base protection layer, a padding layer, and a cover. The base layer is a puncture and cut resistant layer to protect the live actor wearing the Multi-Junctional Bleeding Simulator. The padding layer increases stability and decreases the movement of the Multi-Junctional Bleeding Simulator when worn. The cover provides a uniform look and color to the Multi-Junctional Attachment Unit.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DETAILED DESCRIPTION OF THE INVENTION

Figure 1:
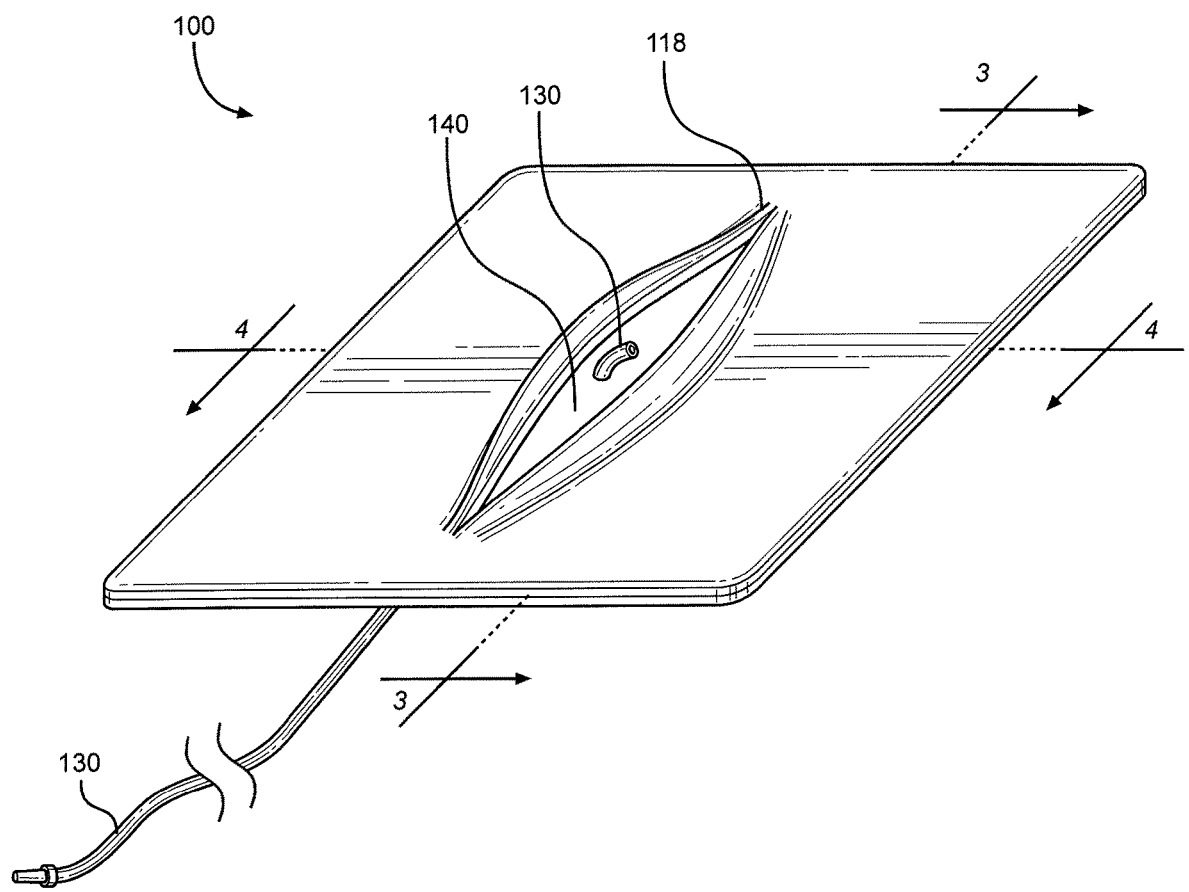
FIG. 1 is a perspective view of the present invention showing a simulated wound with a simulated blood vessel.

Referring initially to FIG. 1, a perspective view of the Multi-Junctional Bleeding Simulator in accordance with the present invention is shown and generally designated 100. The Multi-Junctional Bleeding Simulator 100, when used by a live actor, allows users to safely simulate hemorrhaging in some of the most challenging blood vessels such as the carotid artery, the axillary artery, and the inguinal artery located in the most challenging anatomical locations. The Multi-Junctional Bleeding Simulator 100 provides real-time hemorrhage that can be controlled in real-time by performing the correct hemorrhage control procedures, such as compression and ligation. The Multi-Junctional Bleeding Simulator 100 may be compressed with direct pressure from a person or emergency trauma dressing, may be packed with hemostatic or simple gauze, ligated with hemostats or other ligating instruments or material, and bandaged with pressure dressings to control the simulated hemorrhage. The application of the Multi-Junctional Bleeding Simulator 100 on a live actor allows the live actor to provide the responses and actions of an injured person to provide an additional level of realism that a medical mannequin cannot provide.

Figure 2:
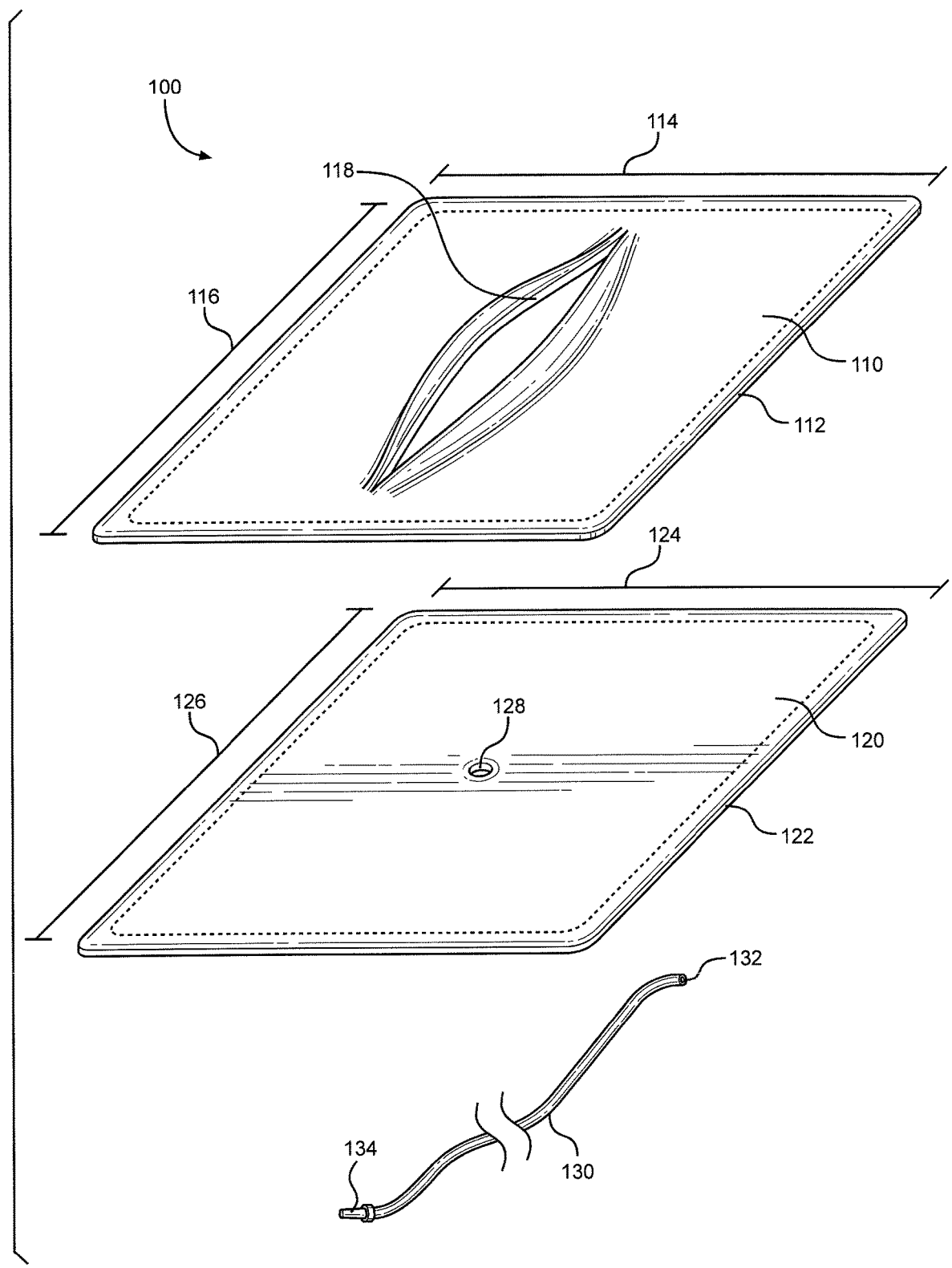
FIG. 2 is an exploded view of the present invention showing a first silicone layer simulating skin with an open wound, a second silicone layer simulating skin, and a silicone tube simulating a blood vessel.

Referring now to FIG. 2, an exploded view of the Multi-Junctional Bleeding Simulator 100 is shown. The Multi-Junctional Bleeding Simulator 100 includes a top silicone layer 110, a second silicone layer 120, and a silicone tube 130. The top silicone layer 110 is constructed of silicone and simulated to look and feel like human skin. This includes manufacturing the top silicone layer 110 with surface texture to mimic certain portions of the human skin and adding color. The top silicone layer 110 has a length 114 and width 116 and a peripheral margin 112. Located approximately in the center of the top silicone layer 110 is an opening 118 constructed to simulate a wound. The wound can be of any variety such as an abrasion, an excoriation, a hematoma, a laceration, an incision, a puncture wound, a contusion, a crushing injury, or a ballistic trauma. In the Multi-Junctional Bleeding Simulator 100, the opening 118 is constructed to simulate a laceration.

The bottom silicone layer 120 is constructed of silicone and simulated to look and feel like human skin similar to top silicone layer 110. The bottom silicone layer 120 has a length 124 and width 126 and a peripheral margin 122. Located off center in the bottom silicone layer 120 is a hole 128 to accommodate the silicone tube 130. The silicone tube 130, having a first end 132 and a second end 134, is inserted through the hole 128 where a small section of the silicone tube 130 adjacent the first end 132 is placed. The location of the opening 118 and the hole 128 is not meant to be limiting and it is contemplated that the location of the opening 118 and the hole 128 may be changed to simulate a particular wound.

The top silicone layer 110 and the bottom silicone layer 120 have the same dimensions. The top silicone layer 110 and the bottom silicone layer 120 are aligned and attached together at their respective peripheral margins 112 and 122 creating a receptacle 140 (shown in FIG. 1) with a volume defined by the surface area of the top silicone layer 110 within the peripheral margin 112 and the surface area of the bottom silicone layer 120 within peripheral margin 122. The ability of silicone to stretch provides a dynamic volume for the receptacle 140 where the maximum volume is at the silicones maximum stretched dimensions. When not stretched, the volume of the receptacle 140 is approximately zero as the top silicone layer 110 lies flat against the bottom silicone layer 120. When stretched, the volume of the receptacle 140 changes to accommodate the needed volume. The receptacle 140 is accessible through the opening 118. The opening 140 also provides access to the section of silicone tube 130 adjacent the first end 132 residing in the receptacle 140.

It is contemplated that the bottom silicone layer 120 may have larger dimensions than the top silicone layer 110, where the peripheral margin 122 of the bottom silicone layer 120 will not align with the peripheral margin 112 of the top silicone layer 110. In this instance the top silicone layer 110 will be attached to the bottom silicone layer 120 where the respective peripheral margins will not align. The volume will be defined by the surface area of the top silicone layer 110 within the peripheral margin 112 and the bottom silicone layer 120 within peripheral margin 112 of the silicone layer. The shape of the top silicone layer 110 and the bottom silicone layer 120 is not meant to be limiting and it is contemplated that the top silicone layer 110 and the bottom silicone layer 120 may be circular, semi-circular, rectangular, quadrilateral, or any other shape needed to simulate a particular wound.

Figure 3:
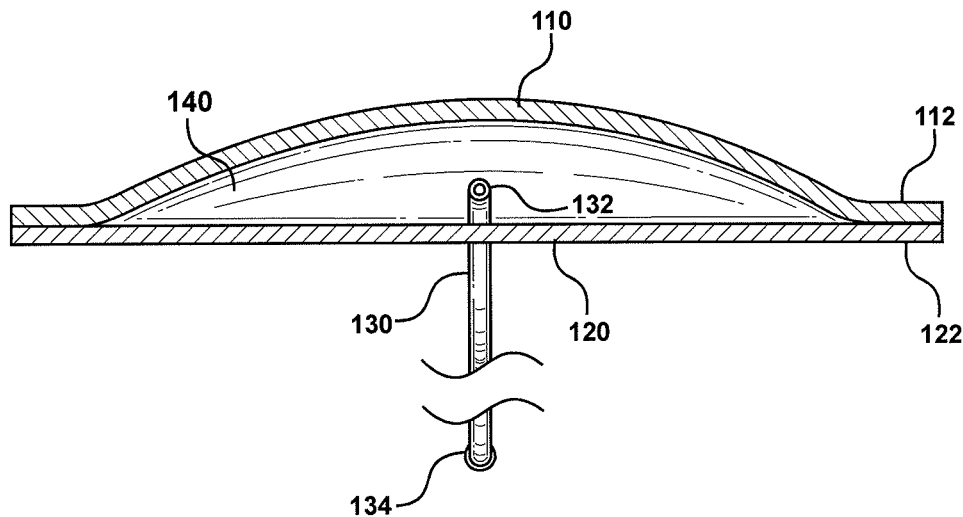
FIG. 3 is a cross-sectional view of the present invention taken along lines 3-3 of FIG. 1.

Referring now to FIG. 3, a cross-sectional view of the Multi-Junctional Bleeding Simulator 100 taken along lines 3-3 of FIG. 1 is shown. As shown, the Multi-Junctional Bleeding Simulator 100 includes the top silicone layer 110 attached to the bottom silicone layer 120 at the peripheral margins 112 and 122, respectively. The top silicone layers 110 and the bottom silicone layer 120 have been stretched to increase the volume of receptacle 140 of the Multi-Junctional Bleeding Simulator 100 to show the first end 132 of silicone tube 130 within the receptacle 140.

Figure 4:
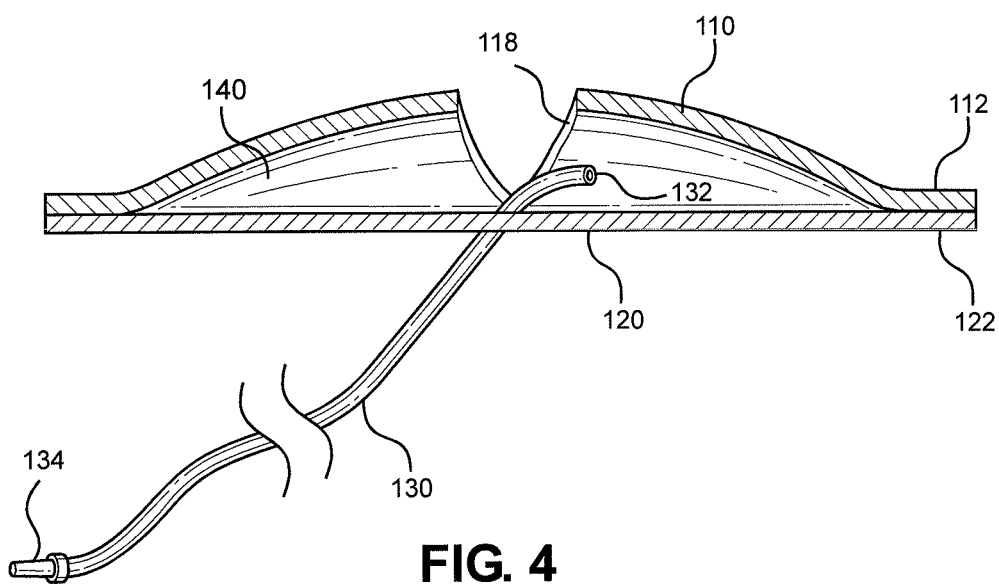
FIG. 4 is a cross-sectional view of the present invention taken along lines 4-4 of FIG. 1.

Referring now to FIG. 4, a cross-sectional view of the Multi-Junctional Bleeding Simulator 100 taken along lines 4-4 of FIG. 1 is shown. As shown, the Multi-Junctional Bleeding Simulator 100 includes the top silicone layer 110 attached to the bottom silicone layer 120 at the peripheral margins 112 and 122, respectively. The top silicone layers 110 and the bottom silicone layer 120 have been stretched to increase the volume of receptacle 140 of the Multi-Junctional Bleeding Simulator 100 to show the first end 132 of silicone tube 130 within the receptacle 140. Opening 118 provides access to the receptacle 140 and the first end 132 of silicone tube 130.

Figure 5:
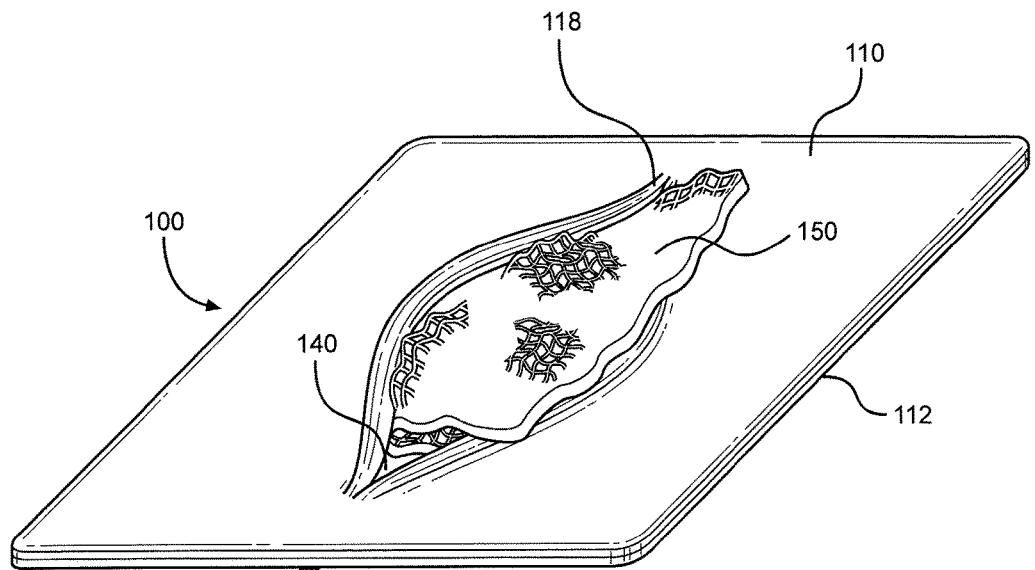
FIG. 5 is a perspective view of the present invention showing the simulated wound compacted with gauze to stop the simulated wound from bleeding.

Referring now to FIG. 5, the Multi-Junctional Bleeding Simulator 100 is shown simulating a hemorrhaging wound. The top silicone layer 110 simulates the skin of a human where the opening 118 simulates an open wound and the receptacle 118 simulates an open cavity. In the Multi-Junctional Bleeding Simulator 100, the silicone tubing may have diameter of approximately 0.5 inches. The first end 132 (not shown) of the silicone tube 130 simulates a ruptured blood vessel within the open the open cavity. The second end 134 of silicone tubing 130 is attached to a blood pumping system capable of flowing simulated blood up to 0.75 liters per minute. The blood pumping system provides a fluid flow of simulated blood in direction 152 into the silicone tubing 130. This provides simulated bleeding through the first end 132 to simulate a hemorrhaging wound where a user may practice the application of gauze 150 to stop a bleeding wound. In particular, the Multi-Junctional Bleeding Simulator 100 may simulate an injury to the carotid artery at the neck junction, the axillary artery at the axillary junction, and the inguinal artery at the inguinal junction.

As shown, the receptacle 140 has been packed with gauze 150 through opening 118 to attempt to stop the bleeding. The use of hemostatic gauze 150 to stop bleeding from hemorrhaging wounds is known in the art and has been implemented in the field for many years. Generally, to stop the bleeding from a traumatic injury using a packing material such as gauze 150, it is recommended that pressure be first applied to the general vicinity of the wound to control the bleeding as the gauze 150 and other supplies are retrieved. Once the gauze 150 and supplies are retrieved, the specific location of the bleed should be identified and direct pressure applied. The wound should then be packed with the gauze 150 until no more gauze 150 may be inserted and then wrapped with pressure dressings to provide pressure on the gauze and wound.

The Multi-Junctional Bleeding Simulator 100 simulates a bleeding wound and may be packed with gauze 150 to stop bleeding in order to train users and prepare them for real world situations. To stop the Multi-Junctional Bleeding Simulator 100 from bleeding using a packing material such as gauze 150, pressure may be first applied to Multi-Junctional Bleeding Simulator 100 over the general vicinity of the opening 118 to control the bleeding as the gauze 150 and other supplies are retrieved. By applying pressure over the general vicinity of the opening 118, the first end 132 of the silicone tube 130 may be compressed making the opening narrow and slowing blood flow out of the silicone tube 130. Once the gauze 150 and supplies are retrieved, the opening 118 may be stretched to access the receptacle 140 to identify the specific location of the bleed, the first end 132 of the silicone tube 130. Direct pressure can then be applied to the first end 132 of the silicone tube 130 to stop bleeding and the receptacle 140 may be packed with gauze 150 until no more gauze 150 can be packed, which should stop the bleeding. To stop the Multi-Junctional Bleeding Simulator 100 from pumping blood into the silicone tube 130, the blood pumping system can be turned off once the procedure is complete or the blood pumping system may be fitted with a pressure sensor that turns off the pumping mechanism when a predetermined pressure in the silicone tube 130 is reached.

Figure 6:
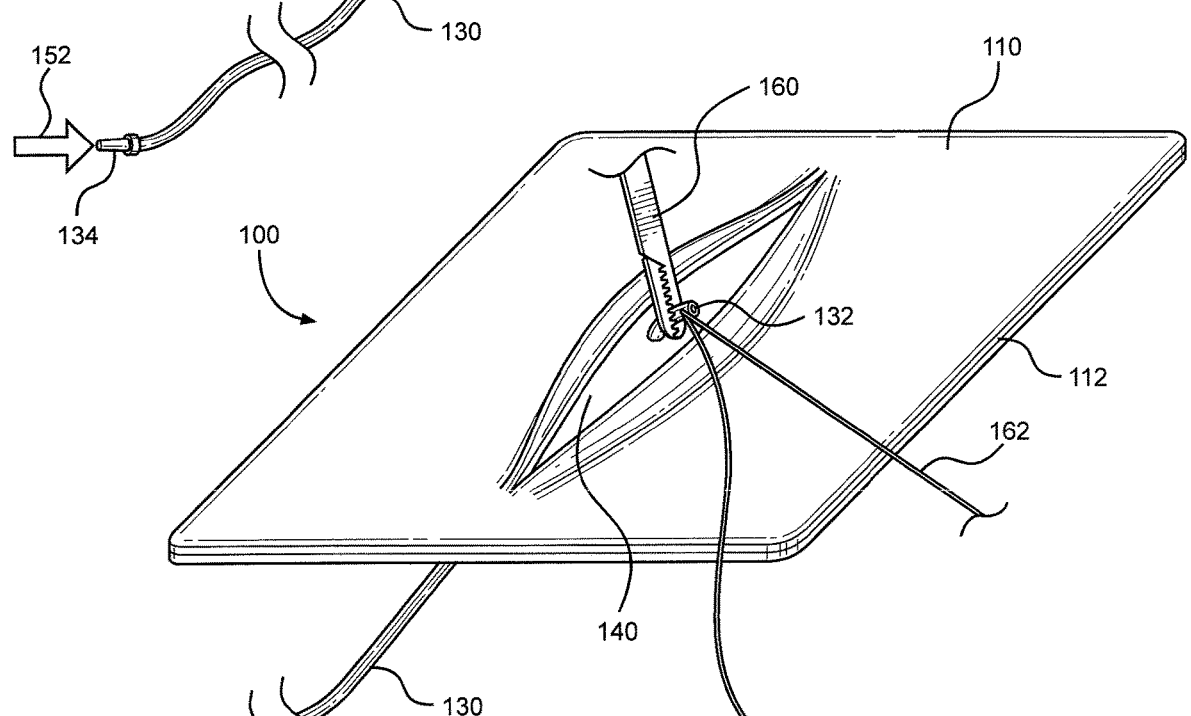
FIG. 6 is a perspective view of the present invention showing the simulated blood vessel being ligated to stop the simulated wound from bleeding.

Referring now to FIG. 6, the Multi-Junctional Bleeding Simulator 100 is shown simulating a hemorrhaging wound. The top silicone layer 110 simulates the skin of a human where the opening 118 simulates an open wound and the receptacle 118 simulates an open cavity. The first end 132 of the silicone tube 130 simulates a ruptured blood vessel within the open open cavity. The second end 134 of silicone tubing 130 is attached to a blood pumping system. The blood pumping system provides a fluid flow of simulated blood in direction 152 into the silicone tubing 130. This provides simulated bleeding through the first end 132 to simulate a hemorrhaging wound where a user may practice the ligation to stop a bleeding wound.

As shown, the first end 132 of the silicone tube 130 has been clamped with a clamp 160 and tied with a suture 162. Ligation to stop bleeding from hemorrhaging wounds is known in the art and has been implemented in the field for many years, but is not as quick, easy, or simple as packing a bleeding wound with gauze to stop the bleeding. Ligation requires more training compared to packing wounds with gauze. Generally, to stop the bleeding from a traumatic injury by ligation, it is recommended that pressure be first applied to the general vicinity of the wound to control the bleeding as a clamp 160, sutures 162, and other supplies are retrieved. Once the clamp 160, sutures 162, and other supplies are retrieved, the wound should be explored to identify the ruptured blood vessel. Once identified, the ruptured blood vessel/s should be clamped with clamp 160 and ligated with sutures 162 to stop the bleeding.

The Multi-Junctional Bleeding Simulator 100 simulates a bleeding wound and may be ligated to stop bleeding in order to train users and prepare them for real world situations. To stop the Multi-Junctional Bleeding Simulator 100 from bleeding by ligating the simulated blood vessel, pressure may be first applied to Multi-Junctional Bleeding Simulator 100 over the general vicinity of the opening 118 to control the bleeding as the clamp 160, sutures 162, and other supplies are retrieved. By applying pressure over the general vicinity of the opening 118, the first end 132 of the silicone tube 130 may be compressed making the opening narrow and slowing down the bleed. Once clamp 160, sutures 162, and supplies are retrieved, the opening 118 may be stretched to access the receptacle 140 to identify the specific location of the bleed, the first end 132 of tube 130. The clamp 160 can then be applied to the first end 132 of the silicone tube 130 to stop bleeding. Once clamped, the first end 132 of the silicone tube 130 may be ligated with sutures 160. To stop the Multi-Junctional Bleeding Simulator 100 from pumping blood into the silicone tube 130, the blood pumping system can be turned off once the procedure is complete or the blood pumping system may be fitted with a pressure sensor that turns off the pumping mechanism when a predetermined pressure in the silicone tube 130 is reached.

Figure 7:
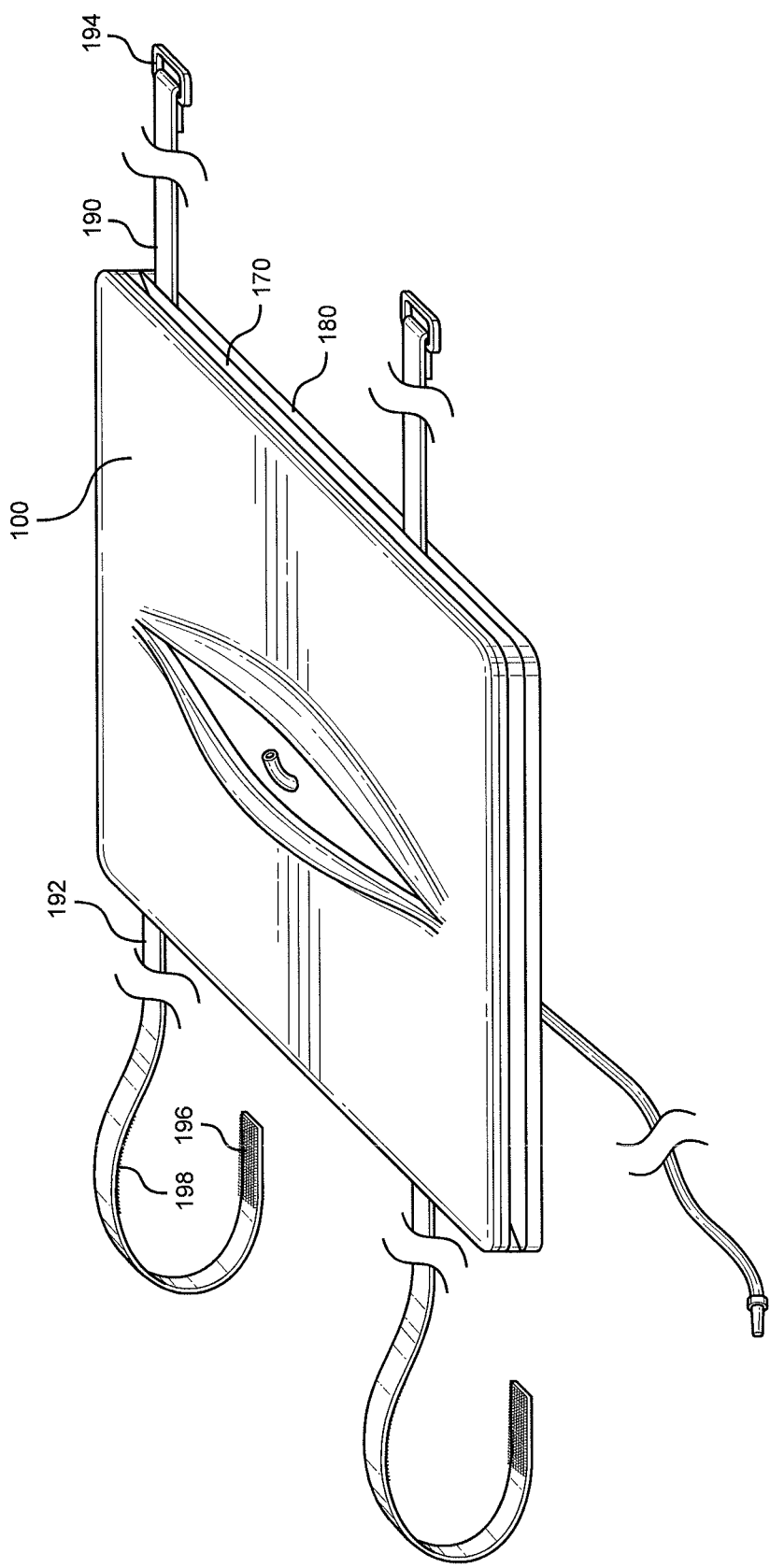
FIG. 7 is a perspective view of the present invention with a protective layer, a padding layer, and securing straps.
Figure 8:
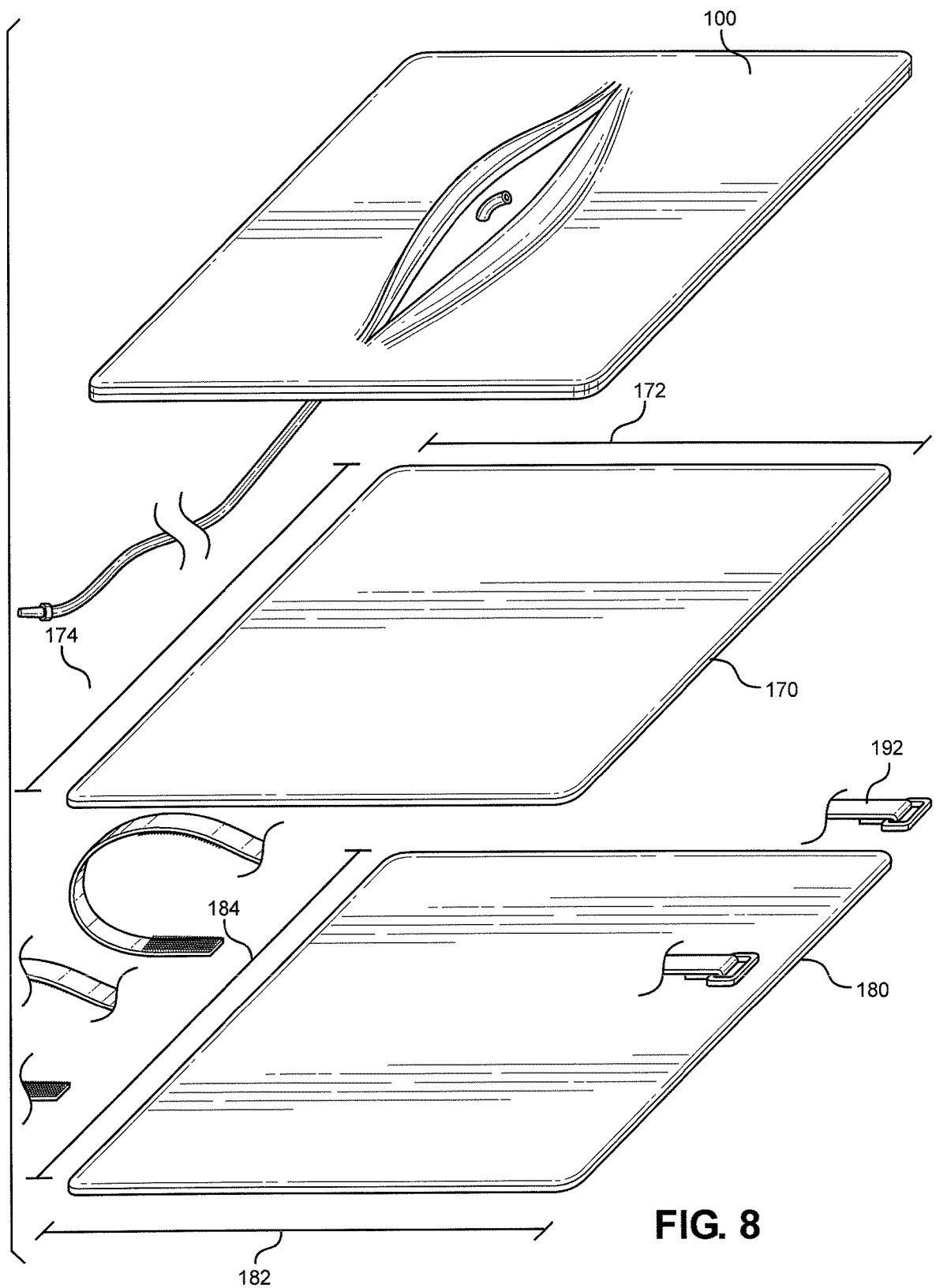
FIG. 8 is an exploded view of the present invention with a protective layer, a padding layer, and securing straps.

Referring now to FIG. 7, the Multi-Junctional Bleeding Simulator 100, described in conjunction with FIG. 8, is shown with a protective layer 170, a layer of padding 180, and securing straps 190. The protective layer 170 has a length 172 and width 174 and is attached to the underside of the Multi-Junctional Bleeding Simulator 100. The protective layer 170 is a layer of ABS with a neoprene coating that is puncture and cut resistant. The protective layer 170 provides a safety barrier to prevent the live actor from being harmed during rigorous training activities. The padding layer 180 has a length 182 and width 184 and is attached to the underside of the protective layer 170. The padding layer 180 contacts and forms itself around the live actor and to provide a friction surface to decrease the movement of the Multi-Junctional Bleeding Simulator 100 when used in dynamic training. The securing straps 190 includes two straps attached to the underside of the protective layer 170, placed between the protective layer 170 and the padding layer 180. Each securing strap 190 includes a strap 192 with a square buckle 194 at one end and a hook portion 196 at the opposite end, with a loop portion 198 adjacent the hook portion 196. This allows for the adjustment of the length of the strap 192 when used to secure the Multi-Junctional Bleeding Simulator 100 to a live actor. It is contemplated that the strap 192 may be fitted with different types of clasps, buckles, and fasteners.

Figure 9:
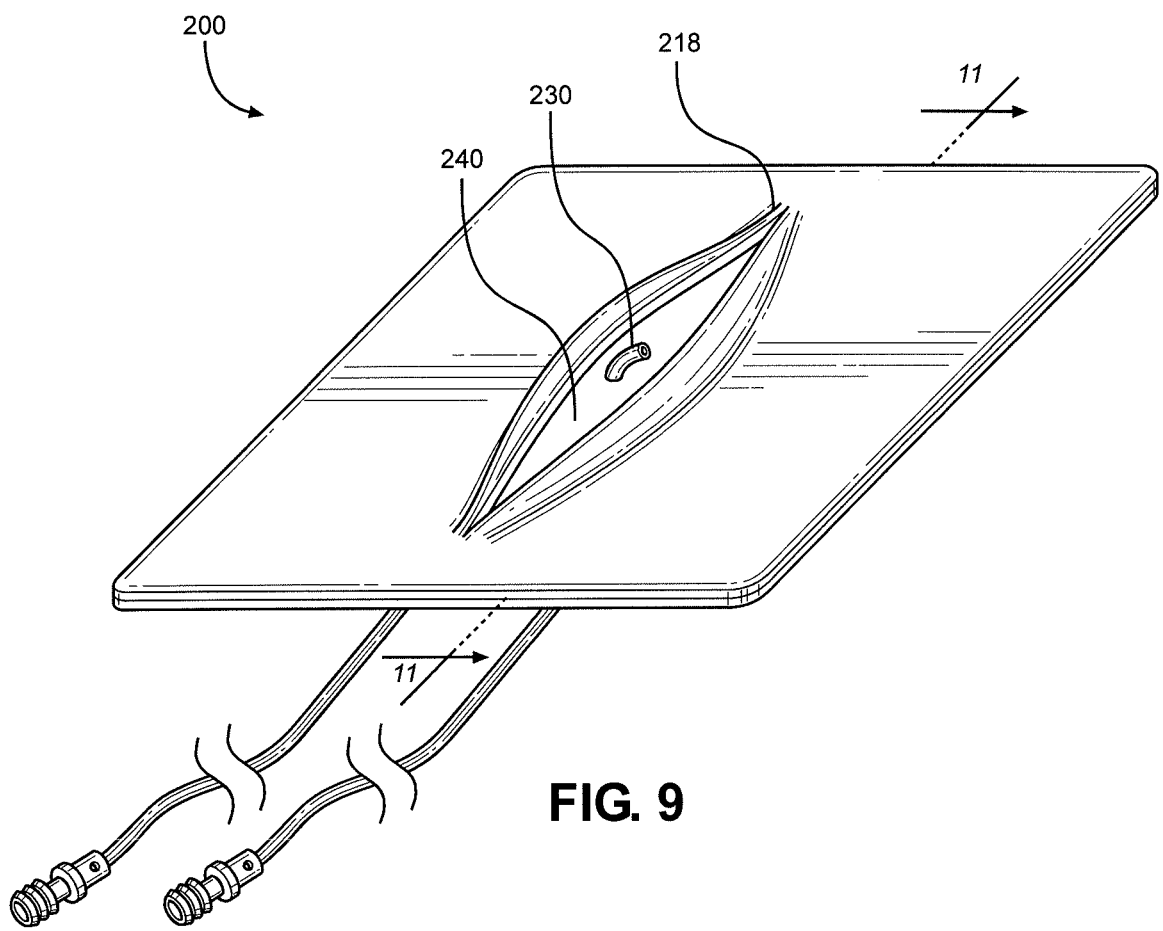
FIG. 9 is a perspective view of an alternative embodiment of the present invention showing a simulated wound with a simulated blood vessel.
Figure 10:
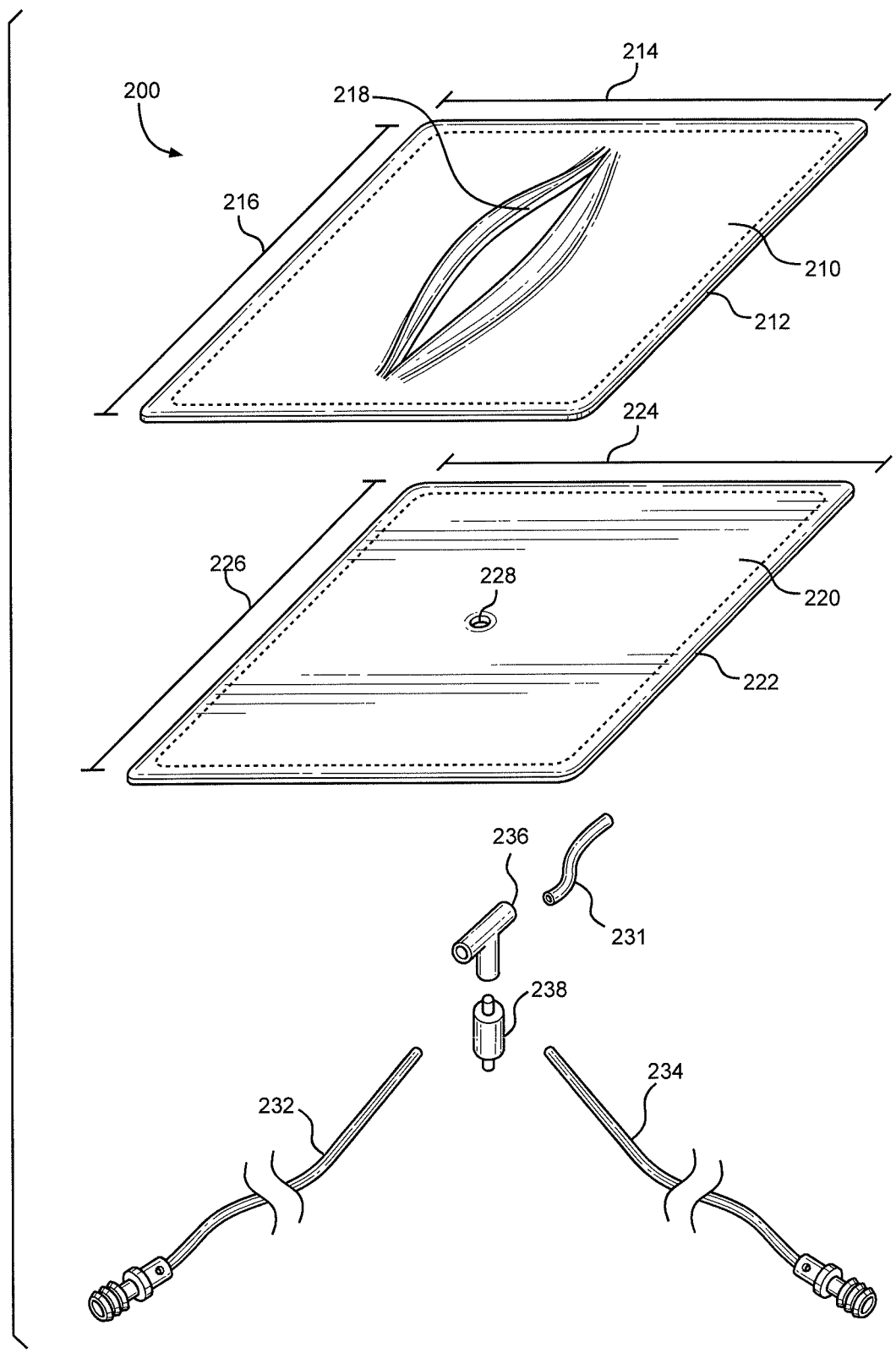
FIG. 10 is an exploded view of the present invention showing a first silicone layer simulating skin with an open wound, a second silicone layer simulating skin, and a tubing system simulating a blood vessel system.

Referring now to FIG. 9, a perspective view of an alternative embodiment of the Multi-Junctional Bleeding Simulator in accordance with the present invention is shown and generally designated 200. The Multi-Junctional Bleeding Simulator 200, described in conjunction with FIG. 10, includes a top silicone layer 210, a second silicone layer 220, and a tubing system 230. The top silicone layer 210 is constructed of silicone and simulated to look and feel like human skin. This includes manufacturing the top silicone layer 210 with surface texture to mimic certain portions of the human skin and adding color. The top silicone layer 210 has a length 214 and width 216 and a peripheral margin 212. Located approximately in the center of the top silicone layer 210 is an opening 218 constructed to simulate a wound. The wound can be of any variety such as an abrasion, an excoriation, a hematoma, a laceration, an incision, a puncture wound, a contusion, a crushing injury, or a ballistic trauma. In the preferred embodiment, the opening 218 is constructed to simulate a laceration. The bottom silicone layer 220 is constructed of silicone and simulated to look and feel like human skin, similar to top silicone layer 210. The bottom silicone layer 220 has a length 224 and width 226 and a peripheral margin 222. Located off center in the bottom silicone layer 220 is a hole 228 to accommodate the tubing system 230.

The top silicone layer 210 and the bottom silicone layer 220 are substantially similar to the top silicone layer 110 and the bottom silicone layer 110 of the Multi-Junctional Bleeding Simulator 100 and are attached in substantially the same way. The top silicone layer 210 and the bottom silicone layer 220 have the same dimensions. The top silicone layer 210 and the bottom silicone layer 220 are aligned and attached together at their respective peripheral margins 212 and 222 creating a receptacle 240 with a volume defined by the surface of the top silicone layer 210 within the peripheral margin 212 and the bottom silicone layer 220 within peripheral margin 222. The ability of silicone to stretch provides a dynamic volume for the receptacle 240. When not stretched, the volume of the receptacle 240 is approximately zero as the top silicone layer 210 lies flat against the bottom silicone layer 220. When stretched, the volume of the receptacle 240 changes. The receptacle 240 is accessible through the opening 218. The opening 218 also provides access to the section of tubing system 230 residing in the receptacle 240.

The tubing system 230 includes a primary tube 231, a feed tube 232 and an exhaust tube 234. The primary tube 231 penetrates through the hole 228 of the bottom silicone layer 220 and resides in the receptacle 240. Attached to the primary tube 231, outside the receptacle 240, is a Y-connector 236. The main branch of the Y-connector 236 is attached to the primary tube 231, the first branch of the Y-connector 236 is connected to the feed tube 232, and a bypass valve 238 is attached to the second branch of the Y-connector 236. Attached to the bypass valve 238 is the exhaust tube 234. The bypass valve 238 is normally closed and fully opens only when a predetermined pressure is met. The bypass valve 238 may also have a cracking pressure which partially opens the bypass valve 238 when pressure is present in the system.

The feed tube 232 is provided with a fluid flow by a blood pumping system. The feed tube 232 provides a fluid flow pathway from the blood pumping system to the first branch of the Y-connecter 236. The bypass valve 238 is normally closed and prevents fluid flow through the second branch of the Y-connecter 236. As a result, the fluid flows through the main branch of the Y-connector 236 and out the primary tube 234 under normal conditions. Under circumstances where the primary tube 234 is restricted, the back pressure in the primary tube 231 may open the bypass valve 238. Depending on the pressure in the primary tube 231, the bypass valve 238 may be either partially open or fully open. In either circumstance, fluid will begin to flow into the exhaust tube 234. Attached to the exhaust tube 234 may be a reservoir (not shown). The reservoir may be transparent or semi-transparent to show that fluid has flowed into the reservoir indicating that the fluid flow through primary tube 231 was restricted.

Figure 11:
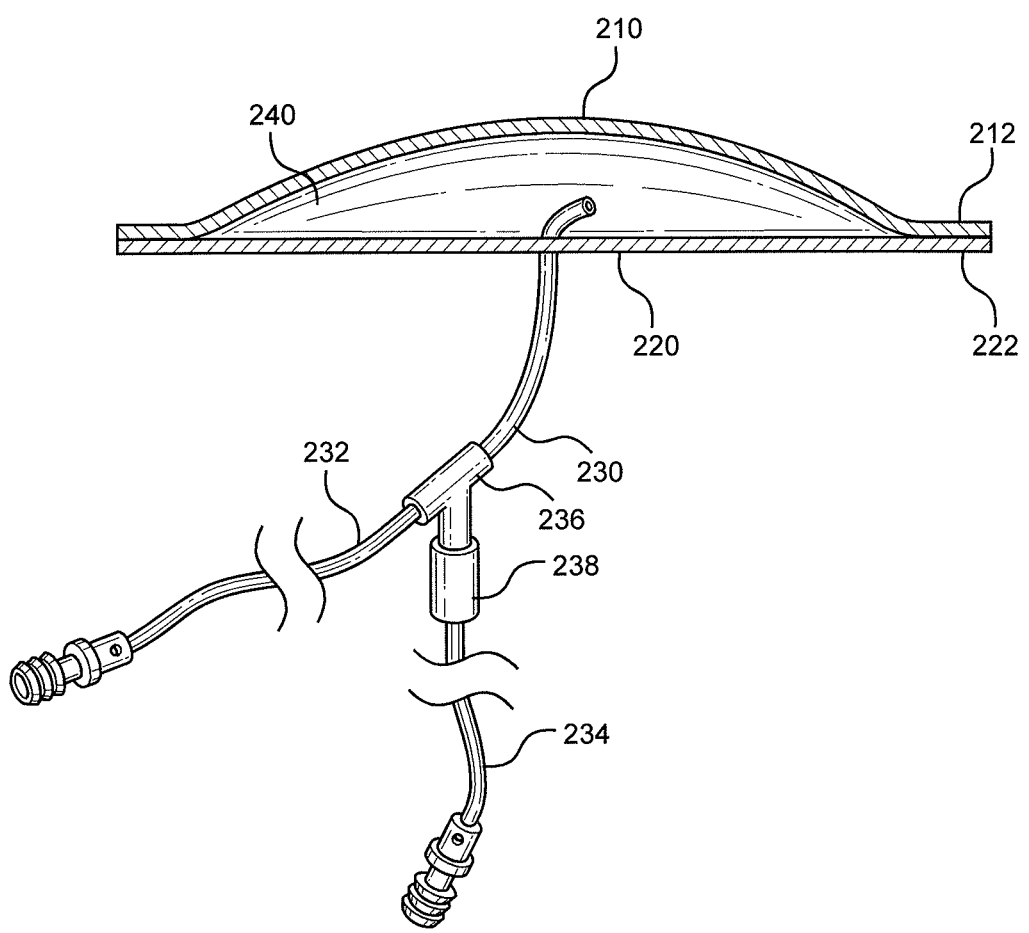
FIG. 11 is a cross-sectional view of the present invention taken along lines 11-11 of FIG. 9.

Referring now to FIG. 11, a cross-sectional view of the Multi-Junctional Bleeding Simulator 200 taken along lines 11-11 of FIG. 9 is shown. As shown, the Multi-Junctional Bleeding Simulator 200 includes the top silicone layer 210 attached to the bottom silicone layer 220 at the peripheral margins 212 and 222, respectively. The top silicone layers 210 and the bottom silicone layer 220 have been stretched to increase the volume of receptacle 240 of the Multi-Junctional Bleeding Simulator 200 to show the primary tube 231 of the tubing system 230 within the receptacle 240.

Figure 12:
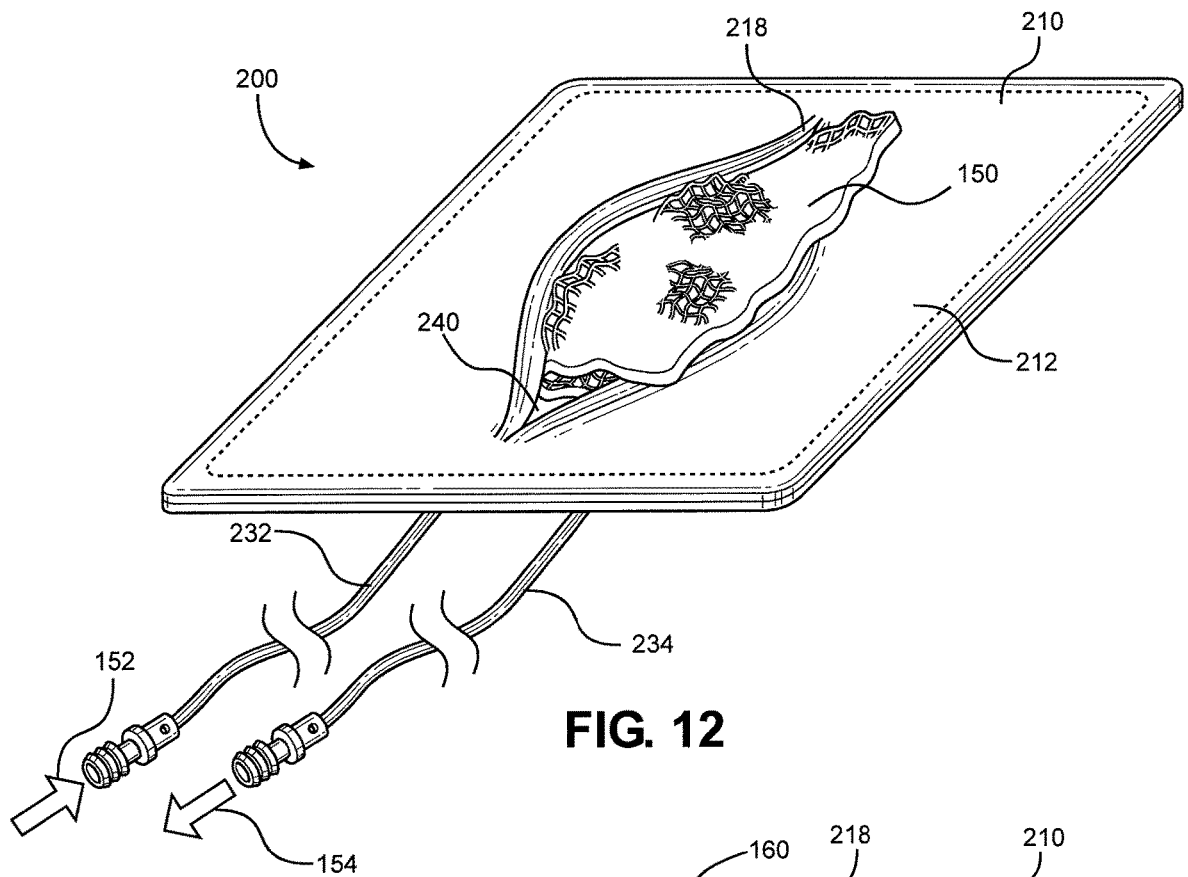
FIG. 12 is a perspective view of the alternative embodiment of the present invention showing the simulated wound compacted with gauze to stop the simulated wound from bleeding.

Referring now to FIG. 12, the Multi-Junctional Bleeding Simulator 200 is shown simulating a hemorrhaging wound. The top silicone layer 210 simulates the skin of a human where the opening 218 simulates an open wound and the receptacle 240 simulates an open cavity. The primary tube 231 (not shown) simulates a ruptured blood vessel within the open cavity 240. The feed tube 232 is attached to a blood pumping system. The blood pumping system provides a fluid flow of simulated blood in direction 152 into the feed tube 232. This provides simulated bleeding through the primary tube 231 of the tubing system 230 to simulate a hemorrhaging wound where a user may practice the application of gauze 150 to stop a bleeding wound.

As shown, the receptacle 240 has been packed with gauze 150 through opening 218 to attempt to stop the bleeding. The Multi-Junctional Bleeding Simulator 200 simulates a bleeding wound and may be packed with gauze 150 to stop bleeding in order to train users and prepare them for real world situations. To stop the Multi-Junctional Bleeding Simulator 200 from bleeding using a packing material such as gauze 150, pressure may be first applied to Multi-Junctional Bleeding Simulator 200 over the general vicinity of the opening 218 to control the bleeding as the gauze 150 and other supplies are retrieved. By applying pressure over the general vicinity of the opening 218, the primary tube 231 of the tubing system 230 may be compressed making the opening narrow. This will create backpressure in the tubing system 230 and will either partially open or fully open the bypass valve 238 to flow fluid through the exhaust tube 234 in direction 154 and into a transparent or semi-transparent reservoir. Fluid flow through the exhaust tube 234 and within the reservoir will indicate to the user that the proper application of pressure was applied to the wound to slow or stop the bleeding.

Once the gauze 150 and supplies are retrieved, the opening 218 may be stretched to access the receptacle 240 to identify the specific location of the bleed, the primary tube 231 of the tubing system 230. When taking the pressure off the general vicinity of the wound, the bypass valve 238 closes and the maximum fluid flow of the fluid flows through the primary tube 231. Once the primary tube 231 is found, due to the flowing fluid, direct pressure can then be applied to the primary tube 231 to stop the bleeding and the receptacle 240 may be packed with gauze 150 until no more gauze 150 can be packed, which should stop the bleeding. If the gauze 150 was properly packed into the wound, the primary tube 231 should be occluded and the bypass valve 238 should be fully open due to the back pressure created by the occluded primary tube 231 meeting the opening pressure of the bypass valve 238. The maximum fluid flow of the fluid flows through the exhaust tube 234 and fills the reservoir, indicating that the wound was properly packed and occluded. If the gauze 150 was not properly packed, the primary tube 231 will still flow fluid indicating that the primary tube 231 was not properly occluded. This will create a marginal amount of back pressure in the tubing system 230. This back pressure will partially open the bypass valve 238 and a slow trickle of fluid flows through the exhaust tube 234 and fills the reservoir, providing an additional indicator that the wound was not properly packed and occluded.

Figure 13:
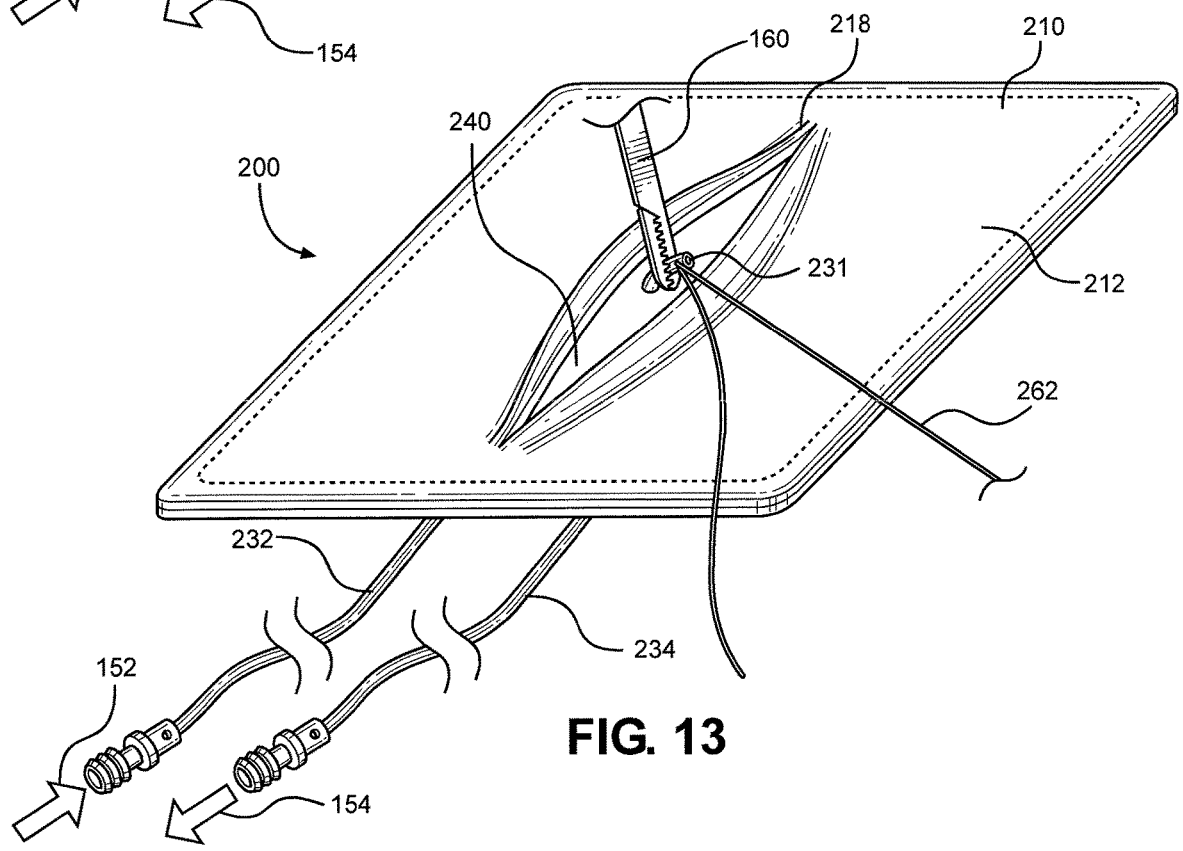
FIG. 13 is a perspective view of the alternative embodiment of the present invention showing the simulated blood vessel being ligated to stop the simulated wound from bleeding.

Referring now to FIG. 13, the Multi-Junctional Bleeding Simulator 200 is shown simulating a hemorrhaging wound. The top silicone layer 210 simulates the skin of a human where the opening 218 simulates an open wound and the receptacle 240 simulates an open cavity. The primary tube 231 simulates a ruptured blood vessel within the open cavity 240. The feed tube 232 is attached to a blood pumping system. The blood pumping system provides a fluid flow of simulated blood in direction 152 into the feed tube 232. This provides simulated bleeding through the primary tube 231 of the tubing system 230 to simulate a hemorrhaging wound where a user may practice ligation to stop a bleeding wound.

As shown, the primary tube 231 has been clamped with a clamp 160 and tied with a suture 162. The Multi-Junctional Bleeding Simulator 200 simulates a bleeding wound and may be ligated to stop bleeding in order to train users and prepare them for real world situations. To stop the Multi-Junctional Bleeding Simulator 200 from bleeding by ligating the simulated blood vessel, pressure may be first applied to Multi-Junctional Bleeding Simulator 200 over the general vicinity of the opening 218 to control the bleeding as the clamp 160, sutures 162, and other supplies are retrieved. By applying pressure over the general vicinity of the opening 218, the primary tube 231 of the tubing system 230 may be compressed making the opening narrow. This will create backpressure in the tubing system 230 and will either partially open or fully open the bypass valve 238 to flow fluid through the exhaust tube 234 in direction 154 and into a transparent or semi-transparent reservoir. Fluid flow through the exhaust tube 234 and within the reservoir will indicate to the user that the proper application of pressure was applied to the wound to slow or stop the bleeding.

Once clamp 160, sutures 162, and supplies are retrieved, the opening 218 may be stretched to access the receptacle 240 to identify the specific location of the bleed, the primary tube 231. The clamp 160 can then be applied to the primary tube 231 to stop the bleeding. Once clamped, the primary tube 231 may be ligated with sutures 160 to stop the bleeding. If the primary tube 231 was properly ligated, the primary tube 231 should be occluded and the bypass valve 238 should be fully open due to the back pressure created by the occluded primary tube 231 meeting the opening pressure of the bypass valve 238. The maximum fluid flow of the fluid flows through the exhaust tube 234 and fills the reservoir, indicating that the wound was properly ligated and occluded. If the suture 162 was not properly applied, the primary tube 231 will still flow fluid indicating that the primary tube 231 was not properly occluded. This will create a marginal amount of back pressure in the tubing system 230. This back pressure will partially open the bypass valve 238 and a slow trickle of fluid flows through the exhaust tube 234 and fills the reservoir, providing an additional indicator that the wound was not properly packed and occluded.

Figure 14:
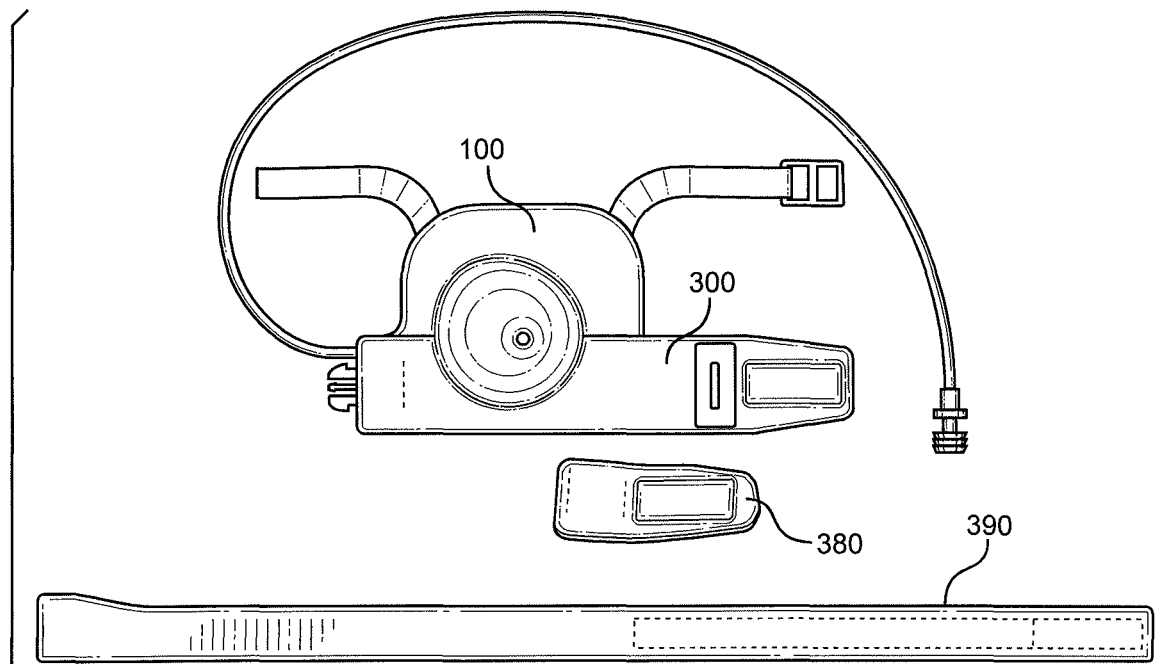
FIG. 14 is a front view of an alternative embodiment of the present invention with a neck strap and an extended strap.
Figure 15:
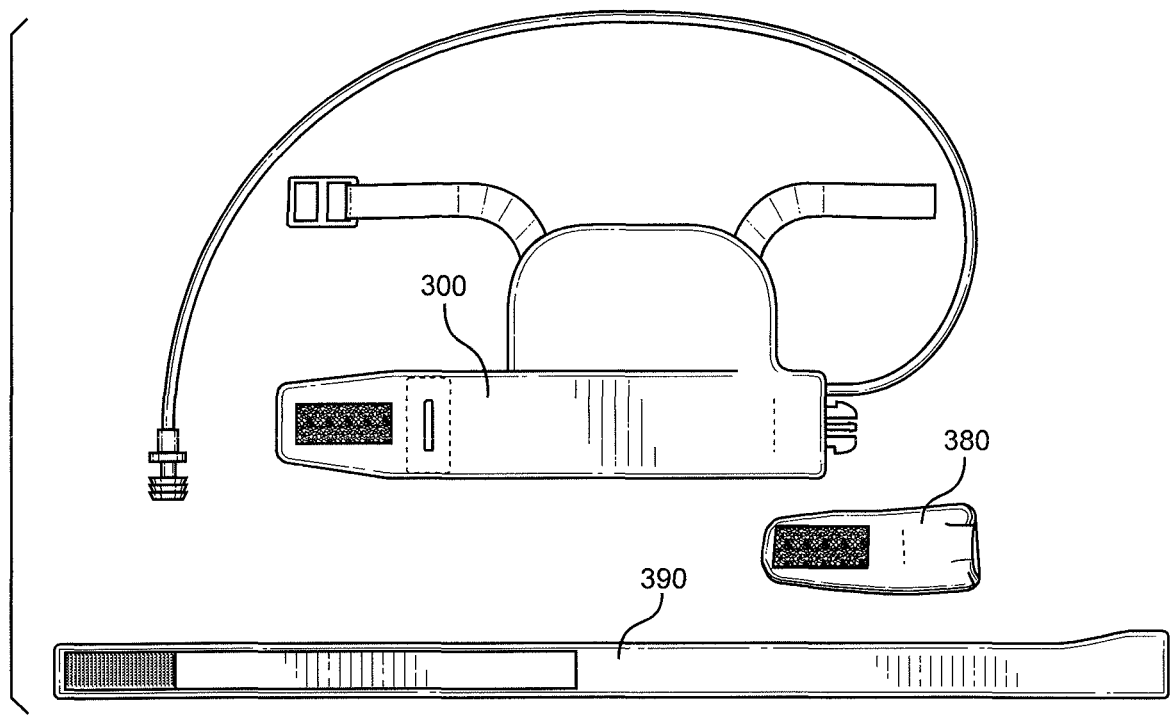
FIG. 15 is a back view of an alternative embodiment of the present invention with a neck strap and an extended strap.

Referring now to FIG. 14, in conjunction with FIG. 15, the Multi-Junctional Bleeding Simulator 100 is with a Multi-Junctional Attachment Unit 300. The Multi-Junctional Attachment Unit 300 includes a neck strap 380 and an extended strap 390. The Multi-Junctional Attachment Unit 300 with either the neck strap 380 or the extended strap 390 provides the ability for the Multi-Junctional Bleeding Simulator 100 to be attached to several different areas of a live actor. The Multi-Junctional Attachment Unit 300 with Multi-Junctional Bleeding Simulator 100 can be worn in one of three positions as follows: the neck junction, the axillary junction, and the inguinal junction. The neck junction is just forward of the junction of the neck and the trunk of the body on both left and right sides. The axillary junction is the junction of the arm and flank around the armpit on both the left and right sides. The inguinal junction is the front side of the junction of the leg and the pelvis to the side of the genital on both left and right sides. The placement of the Multi-Junctional Attachment Unit 300 with Multi-Junctional Bleeding Simulator 100 at the neck junction may simulate a severed carotid artery, the placement at the axillary junction may simulate a severed axillary artery, and the placement at the inguinal junction may simulate a severed inguinal artery, or any other blood vessel in the designated areas.

Figure 16:
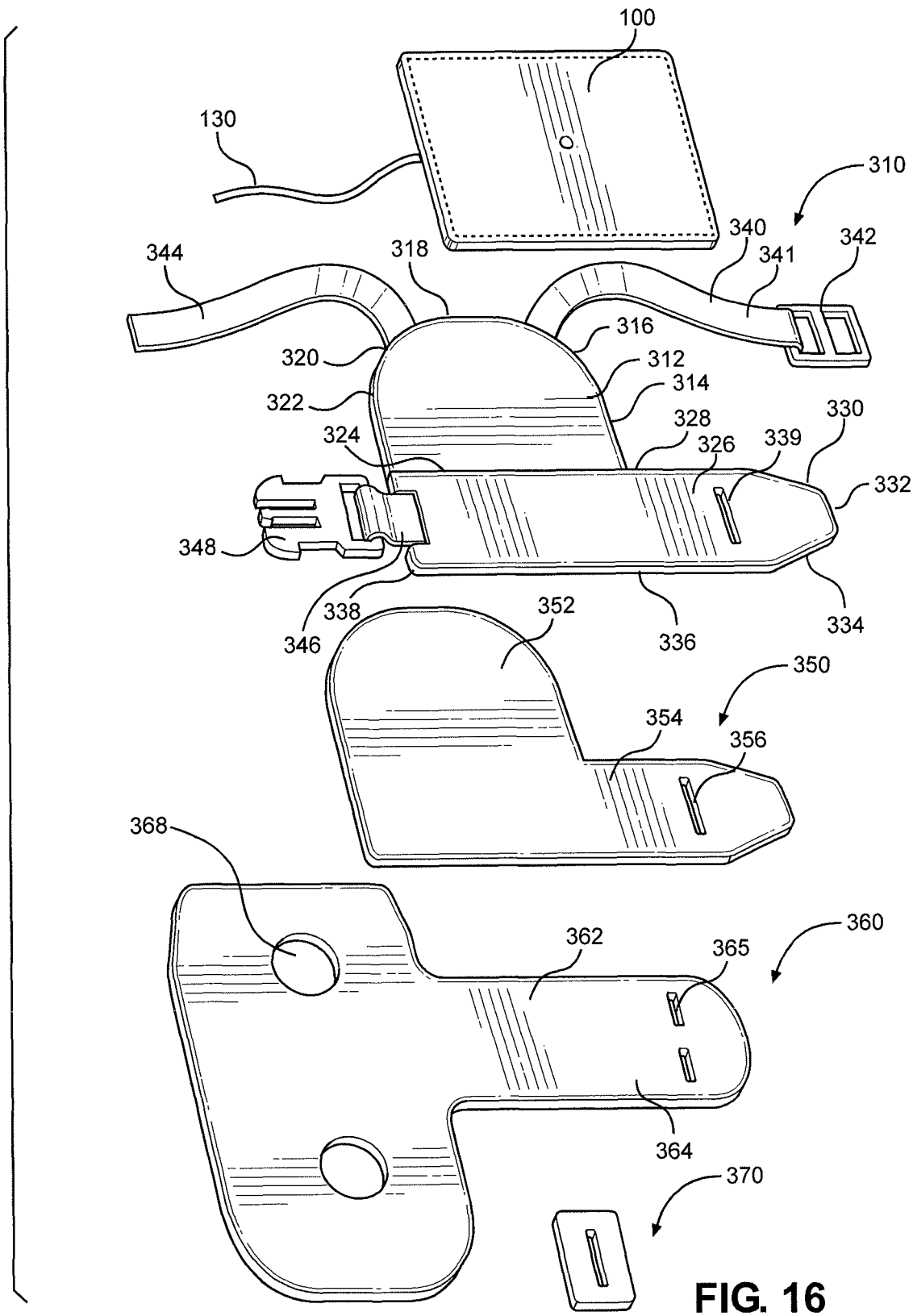
FIG. 16 is an exploded view of the alternative embodiment of the present invention.

Referring now to FIG. 16, an exploded view of the Multi-Junctional Attachment Unit 300 is shown with the Multi-Junctional Bleeding Simulator 100. The use of the Multi-Junctional Attachment Unit 300 with the Multi-Junctional Bleeding Simulator 100 is not meant to be limiting and it is contemplated that the Multi-Junctional Bleeding Simulator 200 or any other embodiment of the invention may be used with the Multi-Junctional Attachment Unit 300. The Multi Junctional Attachment Unit 300 includes a base protection layer 310, a padding layer 350, and a cover 360.

The base protection layer 310 includes an upper portion 312 and a lower portion 326. The upper portion 312 includes a right edge 314, a right curved edge 316, a top edge 318, a left curved edge 320, a left edge 322 and a bottom edge 324. The edges of the upper portion 312 form a rough semi-circular shape. Adjacent the bottom edge 324 of the upper portion 312 is the lower portion 326. The lower portion 326 includes a top edge 328, a top-right tapered edge 330, a right edge 332, a bottom-right tapered edge 334, a bottom edge 336, and a left edge 338. The upper portion 312 and the lower portion 326 are made of ABS plastic with a neoprene coating that is puncture and cut resistant. The upper portion 312 and the lower portion 326 may be made of single sheet of ABS plastic with a score line along the bottom edge 324 of the upper portion and the top edge 328 of the lower portion to allow each portion to easily move independent from the other portion. This provides the flexibility needed of the base protection layer 310 to adapt to several different parts of a live actor. It is also contemplated that the upper portion 312 and the lower portion 326 are separate pieces joined together with a flexible material or other methods to allow the upper portion 312 and the lower portion 326 to move independently from the other.

The base protection layer 310 further includes several fasteners. The adjustable limb strap 340 includes a first strap 341 with a friction buckle 342 attached to the top edge 318 of the upper portion 312 and a second strap 344 attached to the left curved edge 320 of the upper portion. The placement of the limb strap 340 at the upper edges of the upper portion 312 allows the limb strap 340 to strap around the live actors arm or leg depending on the orientation of the Multi-Junctional Attachment Unit 300. Attached to the left edge 338 of the lower portion 326 with an attachment strap 346 is a male slide release buckle 348. The male side release buckle 348 allows the attachment of the neck strap 380 or the extended strap 390 to the Multi-Junctional Attachment Unit 300. Formed into the lower portion 326 adjacent the top-right tapered edge 330 and bottom-right tapered edge 334 is a slot 339 formed to receive the extended strap 390.

The padding layer 350 includes an upper portion 352 and a lower portion 354 formed to have similar dimensions as the base protection layer 310. The padding layer 350 is pliable and does not need to have a score line, or similar, to allow the upper portion 352 to move independently of the lower portion 354. Formed in the lower portion is slot 356 corresponding to the location of slot 339. The padding layer 350 is attached to the underside of the protection layer 310. The Multi-Junctional Bleeding Simulator 100 is attached to the topside of the protection layer 310. The cover 360 covers the assembly with the tube 130 protruding out the left edge 338. The cover 360 includes an upper portion 362 and a lower portion 364, which mirrors the upper portion 362. The upper portion 362 includes a slot 365 corresponding to the location of slots 356 and 339 and an opening 368 corresponding to the location of the opening 118 of the Multi-Junctional Bleeding Simulator 100. A slot reinforcement 370 is attached to slots 365, 356, and 339.

Figure 17:
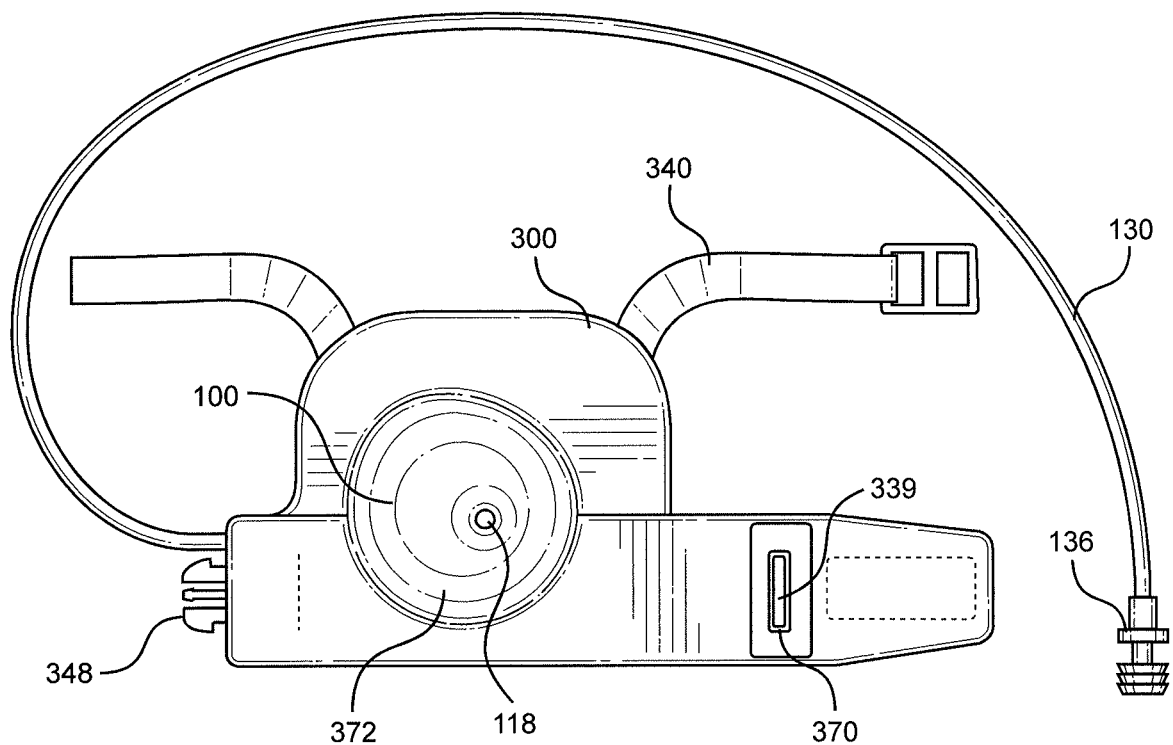
FIG. 17 is a front view of the alternative embodiment of the present invention.

Referring now to FIG. 17, a top view of the Multi-Junctional Attachment Device 300 with Multi-Junctional Bleeding Simulator 100 is shown. As shown, the opening 118 of the Multi-Junctional Bleeding Simulator 100 simulating a puncture wound is exposed through the cover 360. Special effects 372, simulating human skin, is utilized to blend the cover 360 with the Multi-Junctional Bleeding Simulator 100 to provide a seamless transition between the Multi-Junctional Bleeding Simulator 100 and the cover 360. The limb strap 340 and the tube 130 protrude from the cover 360. The tube 130 includes an adapter 136 to connect to a blood pumping system to provide a flow of simulated blood to the wound. By wearing the Multi-Junctional Attachment Device 300 with Multi-Junctional Bleeding Simulator 100 under clothing, a realistic bleeding puncture wound can be presented.

Figure 18:
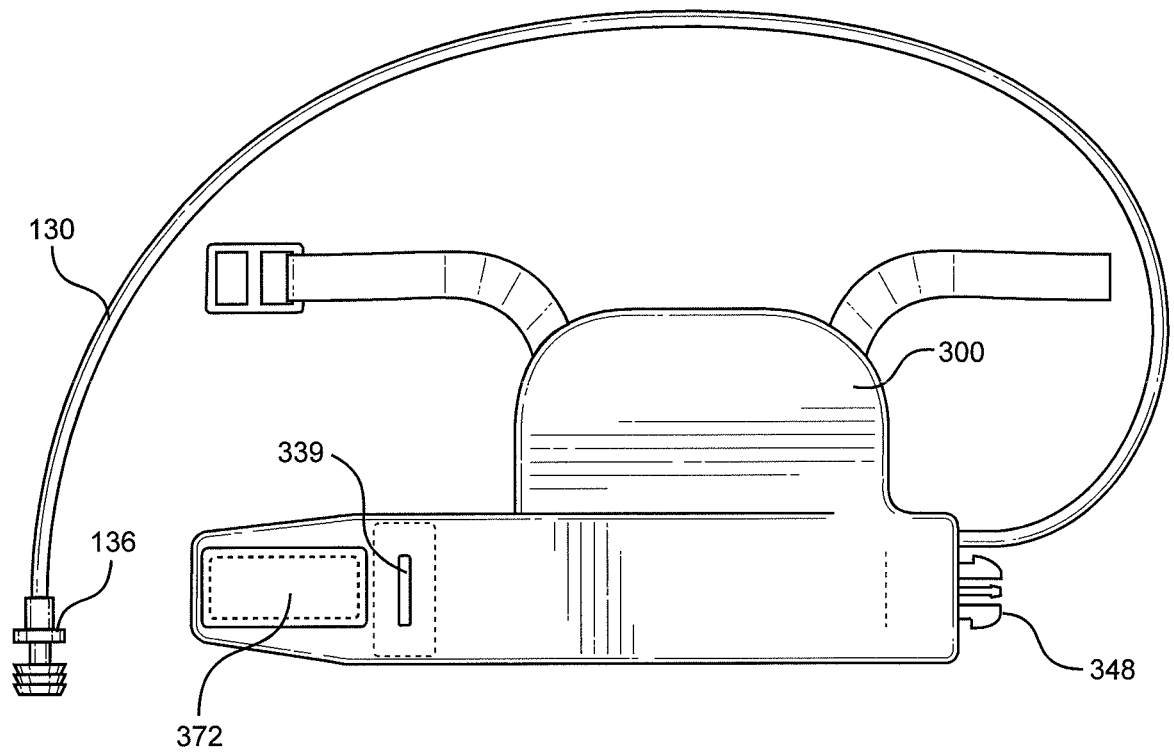
FIG. 18 is a back view of the alternative embodiment of the present invention.

Referring now to FIG. 18, a bottom view of the Multi-Junctional Attachment Device 300 with Multi-Junctional Bleeding Simulator 100 is shown. A hook portion 372 is attached adjacent the slot 339. The hook portion 372 corresponds to a loop portion of the neck strap 380 and the extended strap 390.

Figure 19:
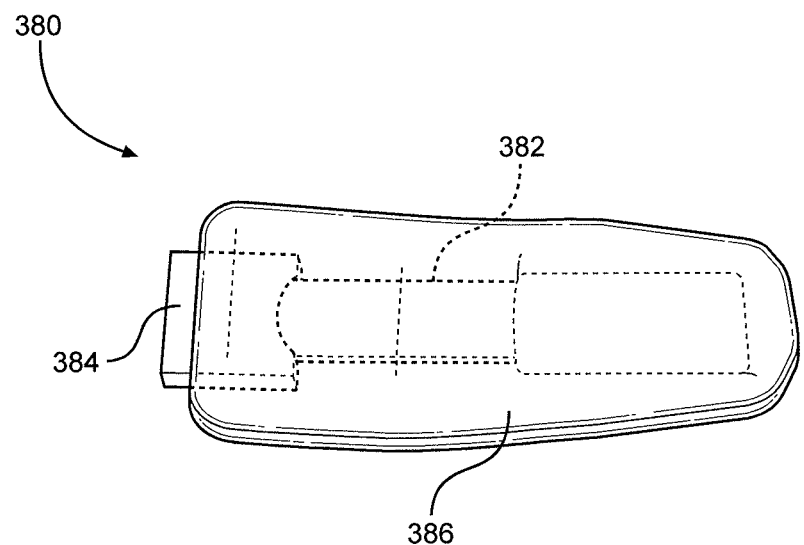
FIG. 19 is a front view of the neck strap of the present invention.
Figure 20:
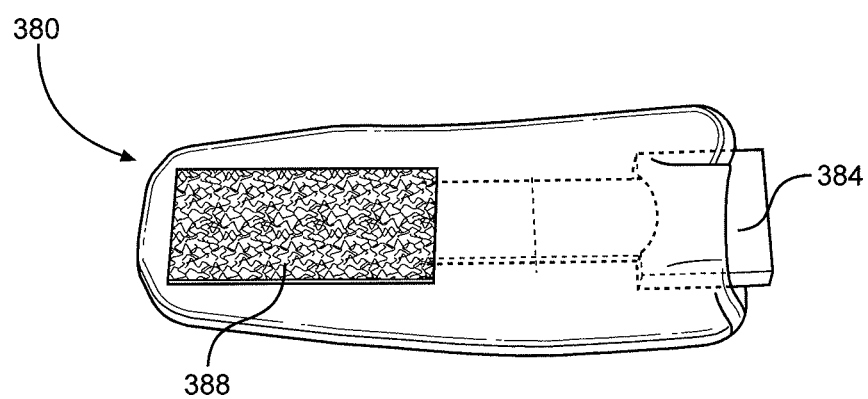
FIG. 20 is a back view of the neck strap of the present invention.

Referring now to FIG. 19 and FIG. 20, the neck strap 380 includes a strap 382 (shown in dashed lines) with a female side release buckle 384 attached to one end. The strap 382 and the female side release buckle 384 are covered by a cover 386. Attached to the strap 382, over the cover 386, and opposite to the buckle 382, is a loop portion 388. The cover 386 is similar to the cover 360.

Figure 21:
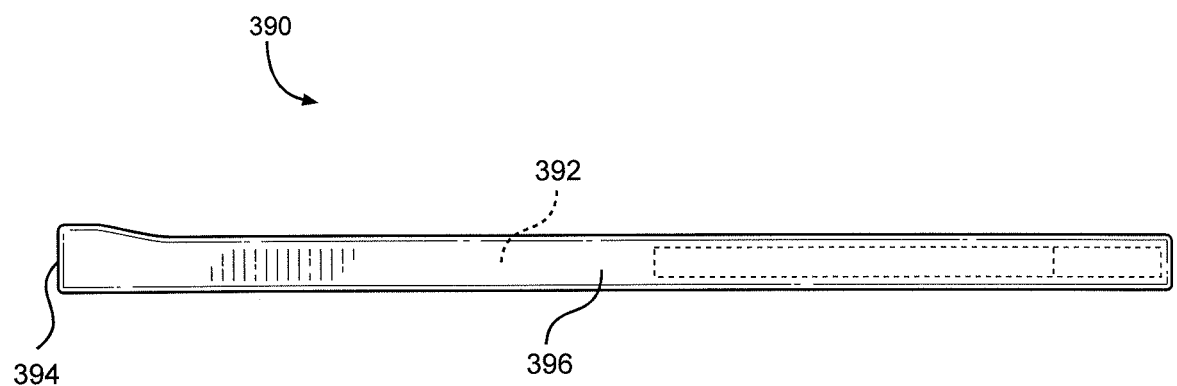
FIG. 21 is a front view of the extended strap of the present invention.
Figure 22:
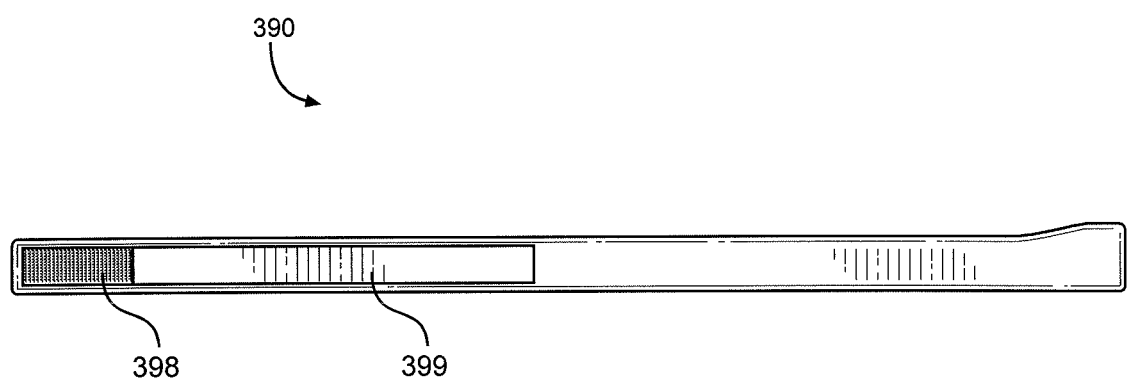
FIG. 22 is a back view of the extended strap of the present invention.
Figure 23:
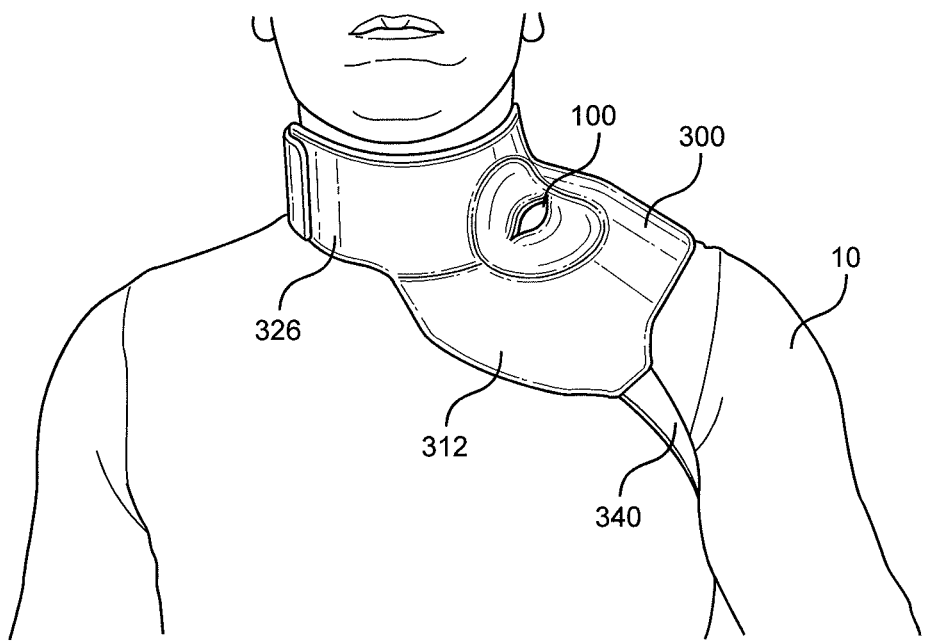
FIG. 23 is a front view of the present invention attached to the neck junction of a live actor.
Figure 24:
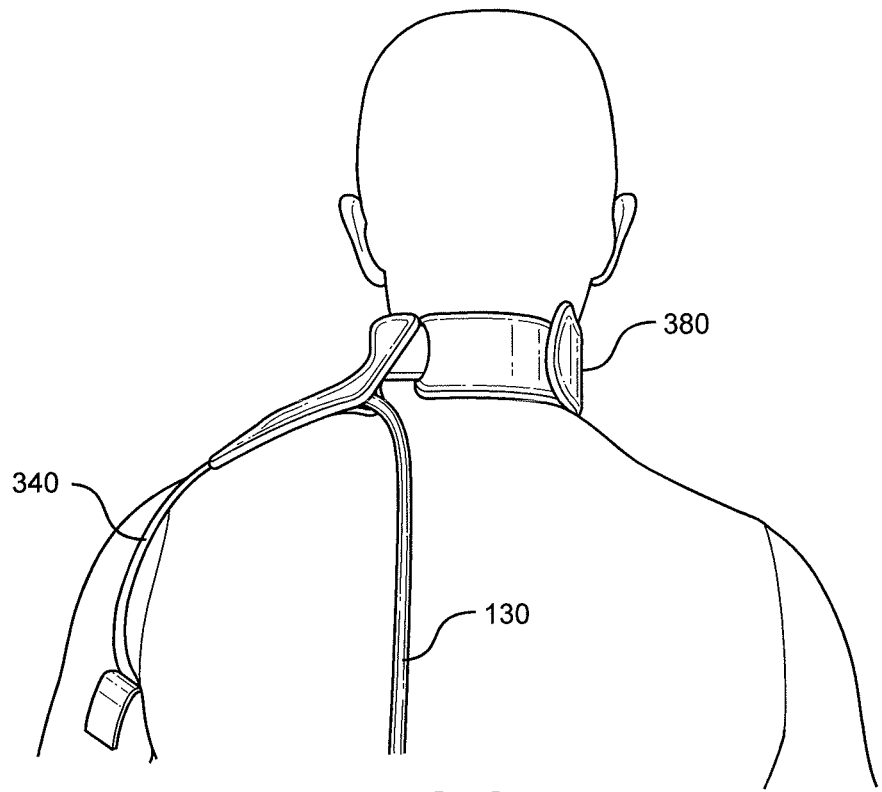
FIG. 24 is a back view of the present invention attached to the neck junction of a live actor.
Figure 25:
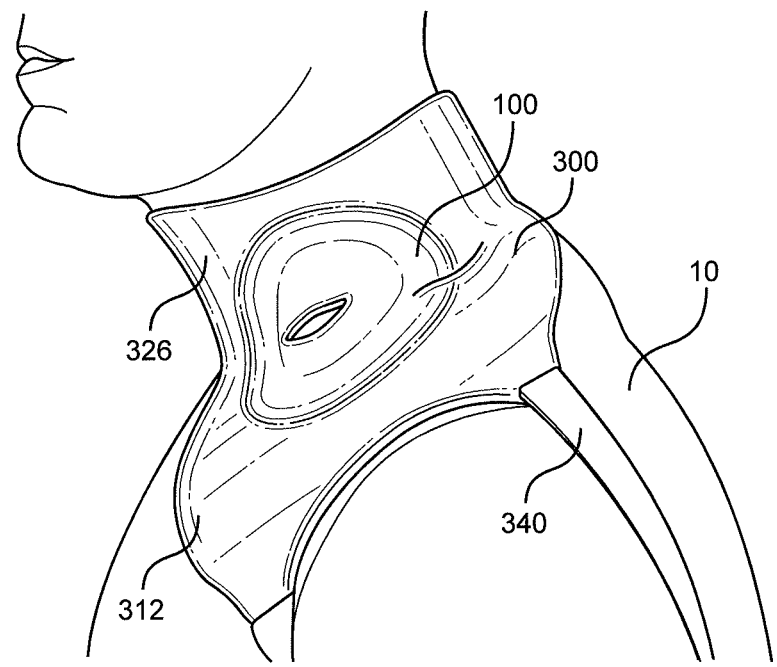
FIG. 25 is a left side view of the present invention attached to the neck junction of a live actor.
Figure 26:
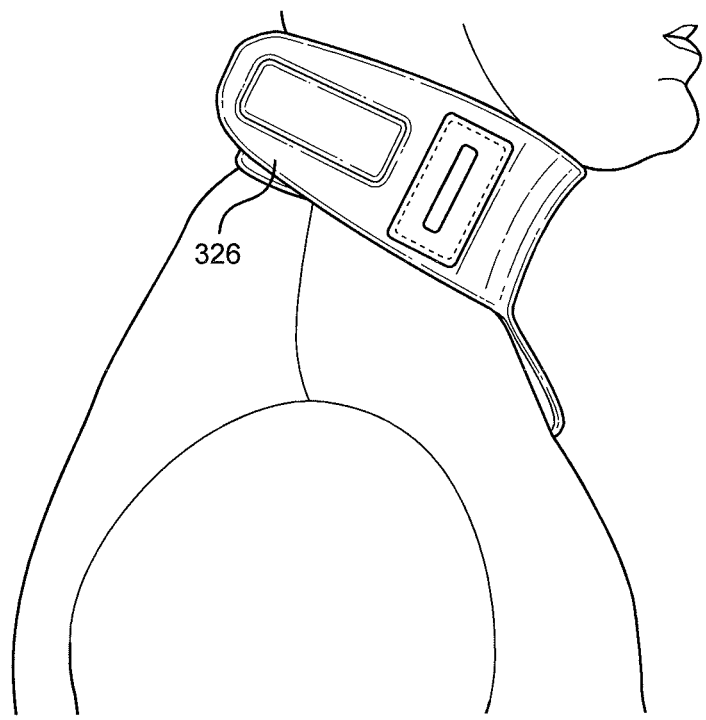
FIG. 26 is a right side view of the present invention attached to the neck junction of a live actor.
Figure 27:
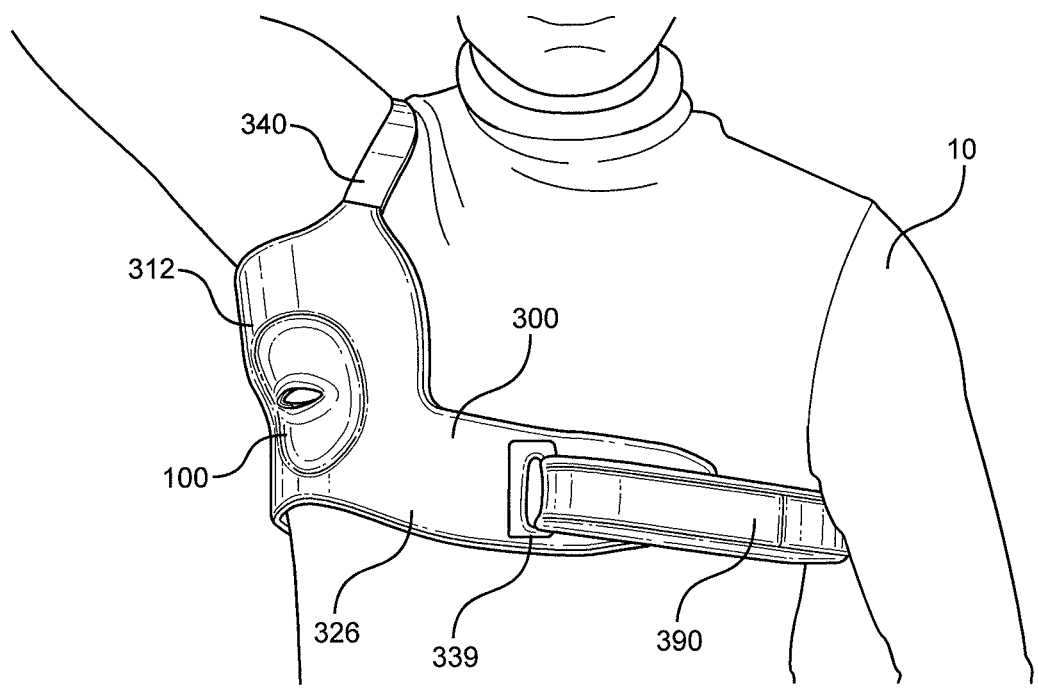
FIG. 27 is a front view of the present invention attached to the axillary junction of a live actor.
Figure 28:
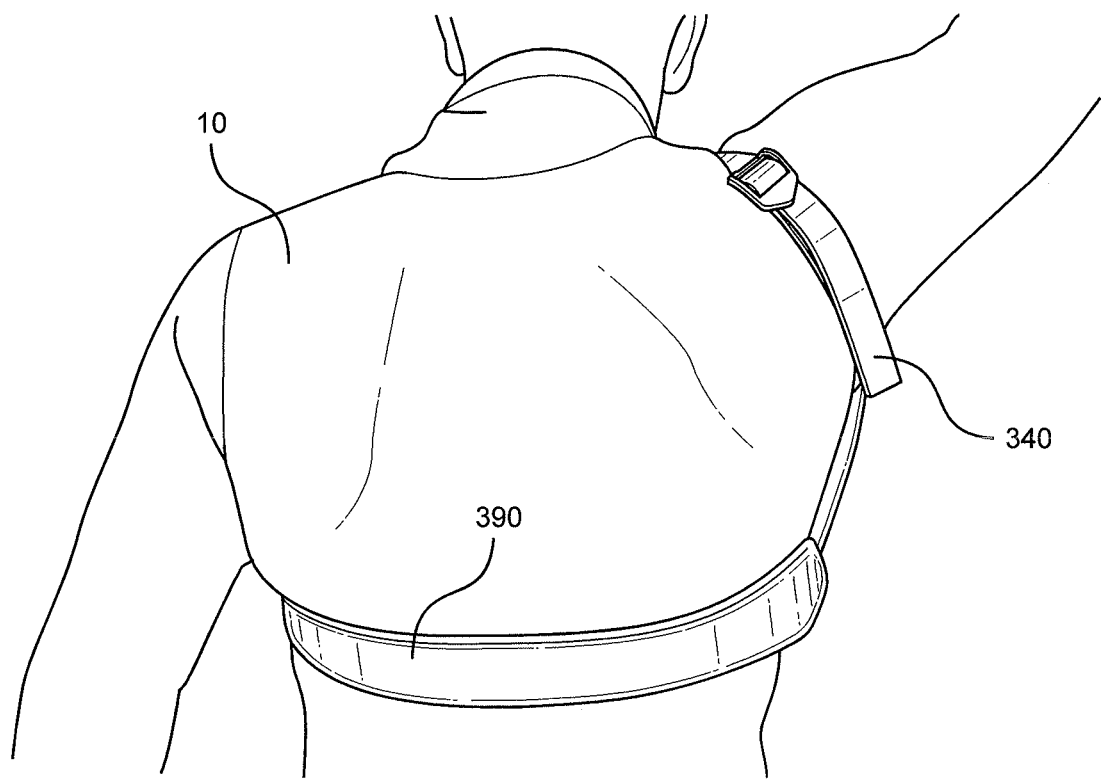
FIG. 28 is a back view of the present invention attached to the axillary junction of a live actor.
Figure 29:
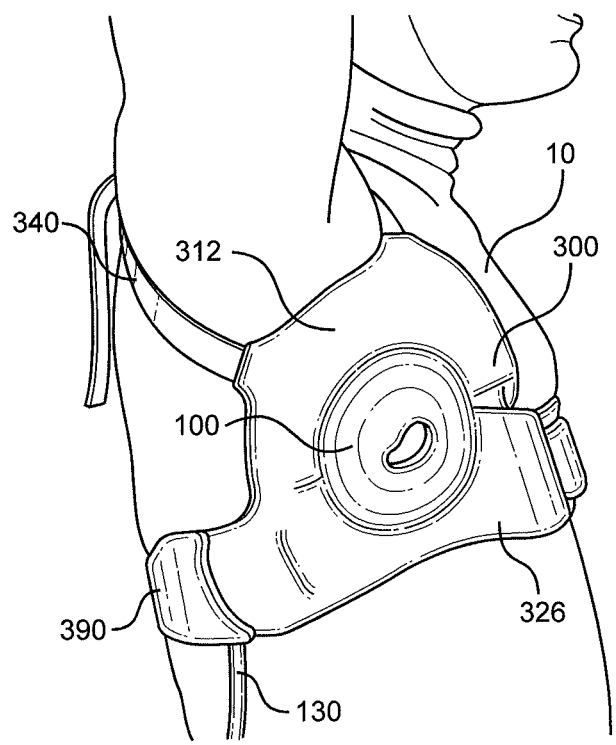
FIG. 29 is a right side view of the present invention attached to the axillary junction of a live actor.
Figure 30:
FIG. 30 is a left side view of the present invention attached to the axillary junction of a live actor.
Figure 31:
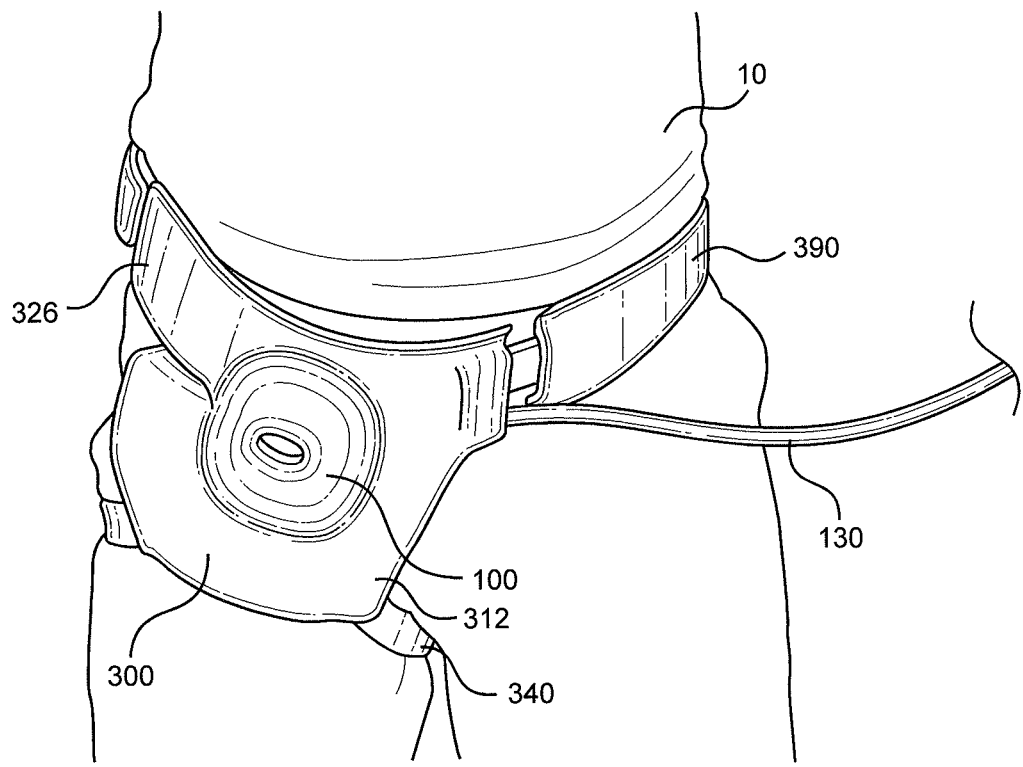
FIG. 31 is a front view of the present invention attached to the inguinal junction of a live actor.
Figure 32:
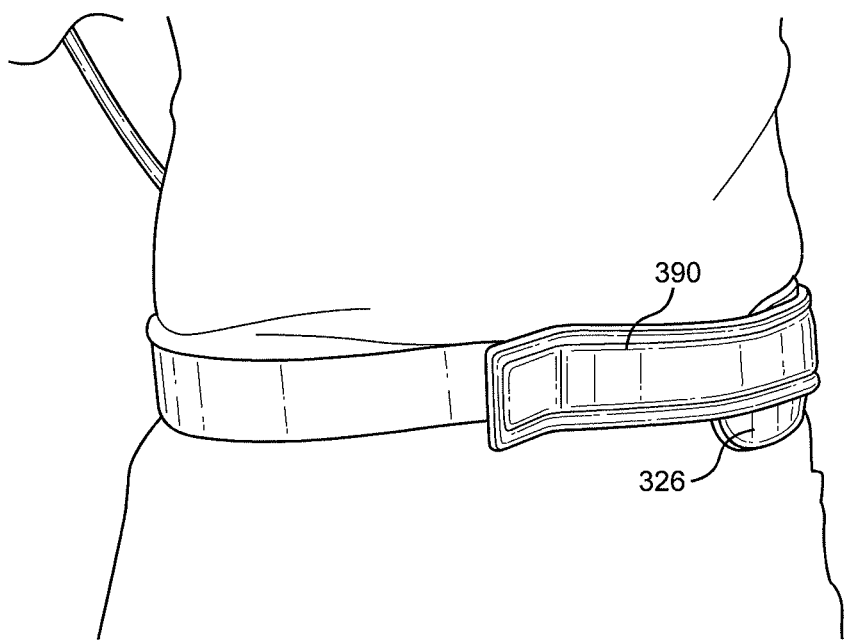
FIG. 32 is a back view of the present invention attached to the inguinal junction of a live actor.
Figure 33:
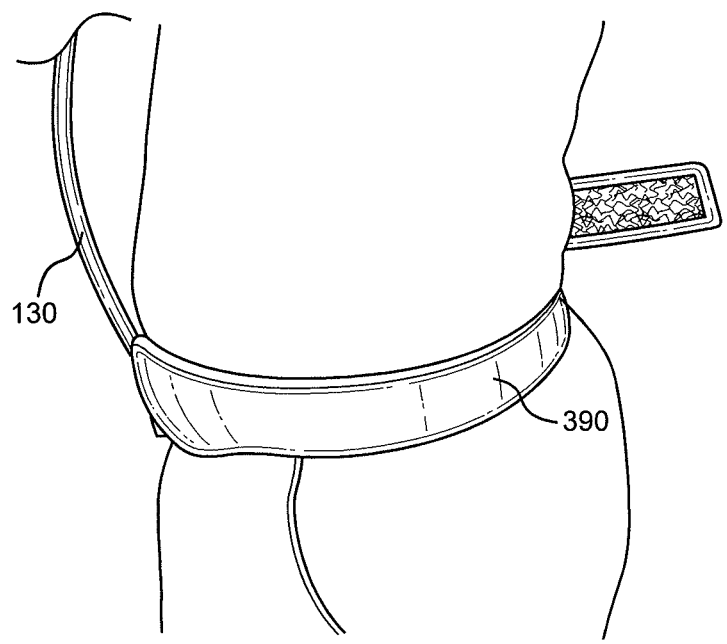
FIG. 33 is a left side view of the present invention attached to the inguinal junction of a live actor.
Figure 34:
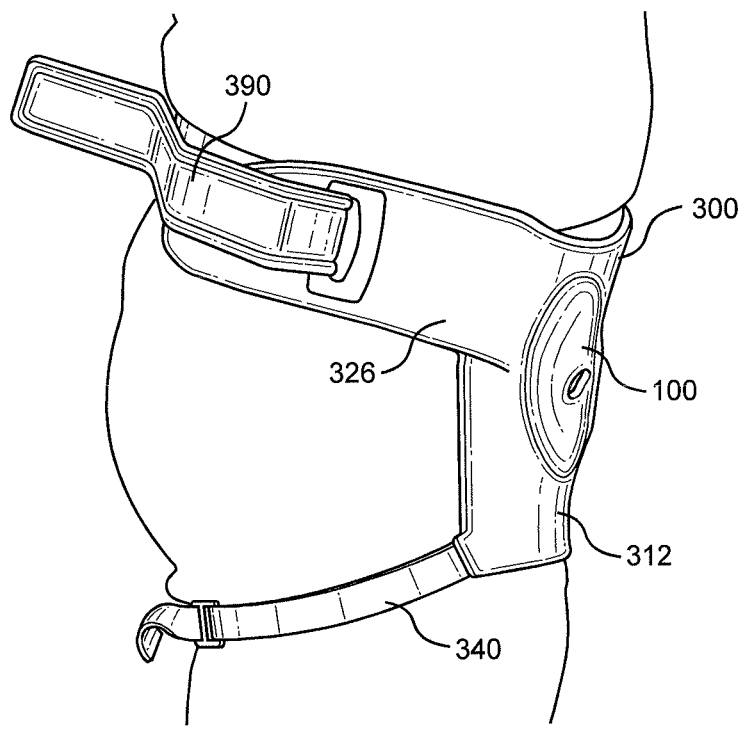
FIG. 34 is a right side view of the present invention attached to the inguinal junction of a live actor.

Referring now to FIG. 21 and FIG. 22, the extended strap 390 includes a strap 392 (shown in dashed lines) with a female side release buckle 394 attached to one end. The strap 392 and the female side release buckle 394 are covered by a cover 396. Attached to the strap 392, over the cover 396, and opposite to the buckle 392, are a loop portion 398 and a hook portion 399. The cover 396 is similar to the cover 360. The extended strap 390 is substantially longer in length than the neck strap 380. The extended strap is utilized to wrap around the torso of a live actor, whereas the neck strap 380 is utilized to wrap around the neck of a live actor.

Referring now to FIGS. 23-26, the Multi-Junctional Attachment Unit 300 with Multi-Junctional Bleeding Simulator 100 is attached at the neck junction of a live actor 10. The female side release buckle 384 of the neck strap 380 is attached to the male side release buckle 348 of the lower portion 326 of the Multi-Junctional Attachment Unit 300 (not shown). The neck strap 380 and the lower portion 326 wraps around the live actor's 10 neck, wherein the hook portion 372 of the lower portion hooks onto the loop portion 388 of the neck strap 380 (not shown). The limb strap 340 is connected to the live actor's 10 arm. This provides a secure attachment of the Multi-Junctional Bleeding Simulator 100 to the neck junction of the live actor 10. The silicone tube 130 is directed towards the back of the live actor 10 where it may be connected to a blood pumping system.

Referring now to FIGS. 27-30, the Multi-Junctional Attachment Unit 300 with attached Multi-Junctional Bleeding Simulator 100 is attached at the axillary junction of a live actor 10. The female side release buckle 394 of the extended strap 390 is attached to the male side release buckle 348 of the lower portion 326 of the Multi-Junctional Attachment Unit 300 (not shown). The extended strap 390 and the lower portion 326 wraps around the live actor's 10 torso, wherein the extended strap 390 is inserted through the slot 339 and the hook portion 399 hooks onto the loop portion 398. The limb strap 340 is connected to the of the live actor's 10 arm. This provides a secure attachment of the Multi-Junctional Bleeding Simulator 100 to the axillary junction of the live actor 10. The silicone tube 130 is directed towards the back of the live actor 10 where it may be connected to a blood pumping system.

Referring now to FIGS. 31-34, the Multi-Junctional Attachment Unit 300 with attached Multi-Junctional Bleeding Simulator 100 is attached at the inguinal junction of a live actor 10. The female side release buckle 394 of the extended strap 390 is attached to the male side release buckle 348 of the lower portion 326 of the Multi-Junctional Attachment Unit 300 (not shown). The extended strap 390 and the lower portion 326 wraps around the live actor's 10 torso, wherein the extended strap 390 is inserted through the slot 339 and the hook portion 399 hooks onto the loop portion 398. The limb strap 340 is connected to the of the live actor's 10 thigh. This provides a secure attachment of the Multi-Junctional Bleeding Simulator 100 to the inguinal junction of the live actor 10. The silicone tube 130 is directed towards the front of the live actor 10 where it may be connected to a blood pumping system.

While there have been shown what are presently considered to be preferred embodiments of the present invention, it will be apparent to those skilled in the art that various changes and modifications can be made herein without departing from the scope and spirit of the invention.

The invention claimed is:

1. A multi-junctional bleeding simulator comprising:
a bottom layer;
a top layer attached to said bottom layer forming a receptacle between said top layer and said bottom layer for receiving a packing material, said receptacle having a minimum volume and a maximum volume;
an opening simulating a wound formed into said top layer and providing access to said receptacle; and
a tubing system inserted though the bottom layer, said tubing system protruding a length inside the receptacle, simulating an exposed blood vessel, said tubing system including
a Y-connector having a main branch, a first branch, and a second branch,
a primary tube in fluid communication with said main branch and extending the length inside said receptacle, simulating the exposed blood vessel,
a feed tube in fluid communication with said first branch, and
a bypass valve in fluid communication with said second branch, wherein said bypass valve is normally closed and opens upon a predetermined pressure; and
wherein simulated blood is provided to said tubing system to simulate a hemorrhaging wound;
wherein obstructing of said tubing system by an operator inhibits the simulated blood from expelling from said wound; and
wherein said simulated blood is provided to said tubing system and flows through said feed tube, said first branch of said Y-connector, said main branch of said Y-connector, and out of said primary tube when said primary tube is unobstructed and flows through said feed tube, said first branch of said Y-connector, said first branch of the Y-connector, and out of said bypass valve when said primary tube is obstructed by the operator.

2. The multi-junctional bleeding simulator of claim 1, wherein said tubing system further comprises an exhaust tube in fluid communication with said bypass valve to provide visual indication of an obstructed primary tube.

3. A multi-junctional bleeding simulator comprising:
a simulated wound configured to expel simulated blood from an opening and configured to receive a packing material to inhibit said simulated blood from expelling from said opening;
a multi-junctional attachment unit attached to the simulated wound to attach the simulated wound onto a wearer, said multi-junctional attachment unit including:
a base protection layer attached to said simulated wound;
a padding layer attached to said base protection layer;
a cover covering said simulated wound, base protection layer, and padding layer, and
a limb strap attached to said base protection layer and configured to be attached around the wearer's limb; and
a neck strap attached to said multi-junctional attachment unit and configured to attach said multi-junctional attachment unit to the wearer's neck.

4. The multi-junctional bleeding simulator of claim 3, further comprising: an extended strap attached to said multi-junctional attachment unit and configured to attach said multi-junctional attachment unit to the wearer's torso.

5. A multi-junctional bleeding simulator comprising:
a simulated wound having
a bottom layer,
a top layer attached to said bottom layer forming a receptacle between said top layer and said bottom layer for receiving a packing material,
an opening simulating a wound formed into said top layer and providing access to said receptacle, and
a tubing system inserted through said bottom layer; and
a multi-junctional attachment unit attached to said simulated wound to attach said simulated wound on to a wearer, said multi-junctional attachment unit including
a base protection layer having an upper portion and a lower portion, said simulated wound is attached to said upper portion and said lower portion,
a male slide release buckle attached to said lower portion of said base protection layer,
a limb strap attached to said upper portion of said base protection layer,
a padding layer attached to said base protection layer;
a cover covering said simulated open wound, said base protection layer, and said padding layer,
a slot through said lower portion of said base protection layer, said padding layer, and said cover, and
a base protection layer hook portion attached to said multi-junctional attachment unit adjacent said slot; and
wherein simulated blood is provided to said tubing system to simulate a hemorrhaging wound, and obstructing of said tubing system by an operator inhibits the simulated blood from expelling from said opening.

6. The multi-junctional bleeding simulator of claim 5, further comprising:
a neck strap having a female slide release buckle at one end and a neck strap loop portion at an opposite end, said neck strap is attached to said multi-junctional attachment unit by connecting said female slide release buckle and said male slide release buckle and configured to attach said multi-junctional attachment unit to the wearer's neck by attaching said neck strap loop portion and said base protection layer hook portion.

7. The multi-junctional bleeding simulator of claim 6, further comprising:
an extended strap having a female slide release buckle at one end and an extended strap loop portion and an extended strap hook portion at an opposite end, said extended strap is attached to said multi-junctional attachment unit by connecting said female slide release buckle and said male slide release buckle and configured to attach said multi-junctional attachment unit to the wearer's torso by sliding said opposite end of said extended strap through said slot and attaching said extended strap loop portion to said extended strap hook portion.

8. The multi-junctional bleeding simulator of claim 7, wherein said tubing system protrudes a length inside said receptacle simulating an exposed blood vessel.

9. The multi-junctional bleeding simulator of claim 8, wherein said tubing system comprises a single conduit.

10. The multi-junctional bleeding simulator of claim 8, wherein said tubing system comprises:
a Y-connector having a main branch, a first branch, and a second branch;
a primary tube in fluid communication with said main branch and extending a length inside said receptacle;
a feed tube in fluid communication with said first branch; and
a bypass valve in fluid communication with said second branch, wherein said bypass valve is normally closed and opens upon a predetermined pressure.

11. The multi-junctional bleeding simulator of claim 10, wherein said tubing system further comprises an exhaust tube in fluid communication with said bypass valve.

12. The multi-junctional bleeding simulator of claim 11, wherein said simulated blood is provided to said tubing system and flows through said feed tube, said first branch of said Y-connector, said main branch of the Y-connector, and out of said primary tube when said primary tube is unobstructed and flows through said feed tube, said first branch of said Y-connector, said second branch of the Y-connector, said bypass valve, and out of said exhaust tube to provide visual indication of said obstructed primary tube when said primary tube is obstructed.

* * * * *